US010688175B2

(12) United States Patent
Carter

(10) Patent No.: US 10,688,175 B2
(45) Date of Patent: Jun. 23, 2020

(54) NSP10 SELF-ASSEMBLING FUSION PROTEINS FOR VACCINES, THERAPEUTICS, DIAGNOSTICS AND OTHER NANOMATERIAL APPLICATIONS

(71) Applicant: Daniel C. Carter, Fayetteville, TN (US)

(72) Inventor: Daniel C. Carter, Fayetteville, TN (US)

( * ) Notice: Subject to any disclaimer, the term of this patent is extended or adjusted under 35 U.S.C. 154(b) by 0 days.

(21) Appl. No.: 15/768,250

(22) PCT Filed: Oct. 13, 2016

(86) PCT No.: PCT/US2016/056904

§ 371 (c)(1),
(2) Date: Apr. 13, 2018

(87) PCT Pub. No.: WO2017/066484

PCT Pub. Date: Apr. 20, 2017

(65) Prior Publication Data

US 2018/0326044 A1 Nov. 15, 2018

Related U.S. Application Data

(60) Provisional application No. 62/240,641, filed on Oct. 13, 2015.

(51) Int. Cl.

| | |
|---|---|
| ***A61K 39/215*** | (2006.01) |
| ***C07K 14/005*** | (2006.01) |
| ***A61K 39/15*** | (2006.01) |
| ***A61K 39/12*** | (2006.01) |
| ***C07K 14/44*** | (2006.01) |
| ***G01N 33/569*** | (2006.01) |
| *A61K 39/00* | (2006.01) |

(52) U.S. Cl.

CPC .............. *A61K 39/15* (2013.01); *A61K 39/12* (2013.01); *C07K 14/005* (2013.01); *C07K 14/44* (2013.01); *G01N 33/56983* (2013.01); *A61K 2039/6031* (2013.01); *A61K 2039/64* (2013.01); *C07K 2319/00* (2013.01); *C12N 2720/12034* (2013.01); *C12N 2740/16034* (2013.01); *C12N 2760/16134* (2013.01); *C12N 2770/20022* (2013.01); *C12N 2770/20034* (2013.01); *C12N 2770/20071* (2013.01); *Y02A 50/383* (2018.01); *Y02A 50/386* (2018.01); *Y02A 50/388* (2018.01); *Y02A 50/39* (2018.01); *Y02A 50/392* (2018.01); *Y02A 50/396* (2018.01); *Y02A 50/41* (2018.01); *Y02A 50/412* (2018.01); *Y02A 50/414* (2018.01); *Y02A 50/466* (2018.01)

(58) Field of Classification Search

None

See application file for complete search history.

(56) References Cited

U.S. PATENT DOCUMENTS

| | | | |
|---|---|---|---|
| 2004/0006001 | A1 | 1/2004 | Carter et al. |
| 2006/0257852 | A1 | 11/2006 | Rappuoli et al. |
| 2009/0087435 | A1 | 4/2009 | Goldbaum et al. |
| 2009/0181046 | A1 | 7/2009 | Cao |
| 2011/0104051 | A1 | 5/2011 | Francis et al. |
| 2011/0311455 | A1 | 12/2011 | Anvari et al. |
| 2012/0301494 | A1 | 11/2012 | Cheng et al. |
| 2013/0167267 | A1 | 6/2013 | Arhancet et al. |

OTHER PUBLICATIONS

International Search Report for PCT/US2016/056904, dated Apr. 21, 2017.

Written Opinion of the International Searching Authority for PCT/US2016/056904, completed Mar. 22, 2017.

Joseph, et al, “Crystal Structure of Nonstructural Protein 10 from the Severe Acute Respiratory Syndrome Coronavirus Reveals a Novel Fold with Two Zinc-Binding Motifs”, Aug. 2006, pp. 7894-7901, vol. 80, No. 16, Journal of Virology.

Su, et al, “Dodecamer Structure of Severe Acute Respiratory Syndrome Coronavirus Nonstructural Protein nsp10”, Aug. 2006, pp. 7902-7908, vol. 80, No. 16, Journal of Virology.

Villeret, et al. “Crystal structure of Pseudomonas aeruginosa catabolic ornithine transcarbamoylase at 3.0-A resolution: A different oligomeric organization in the transcarbamoylase family”, Nov. 1995, pp. 10762-10766, vol. 92, Proc. Natl. Acad. Sci.

*Primary Examiner* — Stacy B Chen

(74) *Attorney, Agent, or Firm* — B. Aaron Schulman, Esq.; Stites & Harbison, PLLC

(57) ABSTRACT

A fusion protein is provided which is based on a self-assembling gene-regulatory NSP10 protein and a protein or peptide capable of being fused to NSP10 without interfering with the assembly or aggregation of the resulting fusion protein. The disclosure also relates to any nanoparticle formed thereby whether complete or not, and methods for the use of the NSP10 fusion protein are also disclosed, including use as vaccines for any indication in humans or animals, therapeutic methods involving the use of the fusion proteins such as using the protein to targeted an antibody or receptor, such as for treating or diagnosing cancer, biosensors using the fusion protein, or the use of the fusion proteins in cell sorting or any imaging application.

17 Claims, 16 Drawing Sheets

Specification includes a Sequence Listing.

(A)

(B)

(A)

(B)

116541 & 116542 – Micro HA

NOTE: Samples were tested in duplicate. HA titer for EN91916 = 16; ar91916 = <2

NSP10 SELF-ASSEMBLING FUSION PROTEINS FOR VACCINES, THERAPEUTICS, DIAGNOSTICS AND OTHER NANOMATERIAL APPLICATIONS

CROSS REFERENCE TO RELATED APPLICATIONS

This application claims the benefit of U.S. Provisional Application Ser. No. 62/240,641, filed Oct. 13, 2015, said application incorporated herein by reference.

FIELD OF THE INVENTION

The present invention relates in general to a fusion protein comprising a self-assembling gene-regulatory NSP10 protein and a protein or peptide capable of being fused to NSP10 without interfering with the assembly or aggregation of the resulting fusion protein. The invention also relates to any nanoparticle formed thereby whether complete or not, the use of the fusion proteins as vaccines for any indication in humans or animals, therapeutic methods involving the use of the fusion proteins such as using the protein to targeted an antibody or receptor, such as for treating or diagnosing cancer, biosensors using the fusion protein, or the use of the fusion proteins in cell sorting or any imaging application.

BACKGROUND OF THE INVENTION

Nanoparticle research is an area of intensive and extensive research, largely due to the changes in physical properties of materials as they approach the 10 nm size range, where among other factors, quantum confinement in semiconductor particles and plasmon resonance can be achieved (Hewakuruppu, et al, 2013). They have a plethora of applications including acting as a semiconductor or sensor, or in biomedical applications as therapeutic agents and vaccines.

Nanoparticles are broadly defined as objects which behave as a single, wholly contained unit with dimensions generally in the range of 1 to 100 nanometers. Their composition is varied and includes a full spectrum of pure or composite materials which can range from metals, such as gold or silver, to biological based particles, such as viruses or engineered virus-like particles (VLP). Typically, virus particles, due to their complexity and requisite storage of genetic information, usually fall toward the upper end of the nanoparticle definition. For example, parvovirus, among the smallest viruses, are particles of approximately 260 Å or 26 nanometers in diameter.

With regard to the prior art, relevant to those biological-based self-assembling nanoparticles (VLP) of non-viral origin, it has previously been disclosed that ferritin, as one such non-viral particle, is the most appropriate and current example of prior art for comparison to the present invention as detailed herein.

The ferritin technology (Carter & Li, 2003; Li, et al., 2006) involves the creation of novel functionalities from an existing naturally occurring and ubiquitous ferritin nanoparticle involved in iron storage. Ferritin is comprised of a small 17 kd protein which self assembles into a spherical 24 unit capsid with a hollow core (FIG. 1). The fortuitous positioning of the N- and C-termini of each subunit on the outer and inner core of the capsid respectively, allows for the engineering of novel materials by standard genetic engineering practices. The surface exposed positions of these termini provide a scaffold to genetically engineer an immense variety of novel nanomaterials with therapeutic, diagnostic and electronic applications. For example, in potential oncology applications, the genetically engineered ferritin containers can be used to house therapeutic drugs and diagnostics, while surface modifications can be used to direct the capsid for highly specific drug delivery or for the creation of new vaccines.

As part of the inventor's early foundational work with ferritin fusion proteins, applications were demonstrated in several areas, including vaccine development (e.g., HIV) and nanomaterial synthesis (e.g., silver single crystals condensed in the core with novel metal binding peptide fusion), as well as demonstration of solution plasmon resonance (Kramer, et. al, 2004). The present inventor observed, and now many others have confirmed, the ease, rapidity and relatively inexpensive process with which these fusion products can be made using standard recombinant techniques and a full spectrum of industry standard prokaryotic and eukaryotic expression systems. Ferritins with novel functionalities can be made and examined in as little as 10 days and modern high-throughput methods allow for the potential production of dozens of these genetic constructs in parallel.

In the vaccine application alone, there are broad and far reaching implications for the successful outcome in a variety of deadly diseases, many which are endemic throughout the world, including influenza and the promise of the long awaited HIV vaccine. To this end, NIH researchers have contributed an additional beautiful example of the effectiveness of this technology in animals against H1N1 influenza (Kanekiyo et al, 2013). In an issue of Science Magazine, the prior ferritin technology has been heralded as the answer to the long awaited universal flu vaccine ("Once-in-a-Lifetime Flu Shot?" Science Vol 341: pg. 1171, September, 2013) (FIG. 2). Clearly, the great potential of the ferritin non-viral nanoparticle platform (Carter & Li, 2003) has been validated independently by a number of research groups around the world.

The protein known as non-structural protein 10 or NSP10 is a viral regulatory protein found in at least the Group I, II and III coronaviruses. The three-dimensional atomic structure of NSP10 from the SARS coronavirus was determined by Su, et al., (2006) (FIG. 3). See also Joseph et al. (2006). This is an approximate 17 Kd MW viral gene regulatory/replicase-inhibitor protein that binds to the host cell 40S ribosomal unit and inhibits translation of host proteins. By suppressing host cell expression, NSP10 facilitates the production of its own viral gene expression.

Structurally, NSP10 is categorized as a zinc finger protein and can be further described as a two subdomain structure with one n-terminal helical subdomain (subdomain I) and one c terminal small beta sheet subdomain (subdomain II). NSP10 normally self-assembles into a spherical dodecamer having trigonal 32 point symmetry with an outer diameter of approximately 84 Å and an inner hollow hydrophobic chamber of 36 Å in diameter (FIGS. 3 & 4) (Su, et al., 2006; PDB identifier: 2G9T, sequence identifier P0C6U8). Subdomains I self-associate to form a trimer interaction at the four capsid n-terminal three-fold axes and subdomains II self-associate as trimeric units on the four c-terminal three-fold axes. One zinc binding site occurs at the interface between the two subdomains, and the three other zinc sites are located within subdomain II near the c-terminus.

NSP10 remains a unique topological representative of a structurally distinct assembling family of proteins, despite almost a decade since its first discovery. There have only been implied sequence homologies with other proteins, such as the HIT-type zinc finger proteins identified through sequence homology by Su, et al. (2006) (FIG. 5) which are also believed to be involved in gene regulation. Given the identified gene regulatory role of this protein, it would be understood that other topologically similar proteins exist, and thus by referring to NSP10, this includes other proteins that have the same physical folds, dimensions or properties, and are NSP10-like (or "NSPL"). In addition, NSP10 as used in the present application refers to other proteins having the same properties of folding and self-assembly as the NSP10 protein. Other proteins usable in the present invention will have sequence homology with the NSP10 protein in varying degrees, such as any level of 45% sequence homology of higher, e.g., 50% homology, 55% homology, 60% homology, 65% homology, 70% homology, 75% homology, 80% homology, 85% homology, 90% homology, 95% homology, or higher. The NSP10 proteins of the invention will thus include those proteins that may not have at least 45% sequence homology, but which contain similar binding regions and bonding patterns such that the self-assembly of the molecule forms the same pattern as the NSP10 fusion protein.

It is thus possible to develop alternate amino acid sequences of NSP10 proteins and accomplish the same objectives of the invention described herein. For example, it would be understood that amino acid substitutions to increase stability, remove zinc binding or change the amino acids exposed in the interior, would be considered within the scope of the invention as set forth below provided that the NSP10 self-assembles as indicated above. As a detailed example, the NSP10 proteins of this invention constitute a family of proteins that have important inter-subunit contacts which occur at the 2 folds of the capsid. Here, the main surface interaction is between two beta sheets running antiparallel (FIG. 6). If necessary or desirable, such features call for the improvement of capsid stability by replacing Met 44 on each protein by cysteine to potentially form a cross-linking disulfide bridge between two fold related dimers. The intermolecular distance between these two residues is approximately 6.2 Å. In the same line of reasoning, one may also potentially substitute a cysteine at or near Valine 42 which could potentially form a disulfide with Cysteine 46 of the adjacent molecule. In any case, it would be readily possible without undo experimentation to create a nanoparticle with increased stability by cross linking the protein in this manner, whether at the two-fold, or elsewhere on the molecule.

Moreover, very recent advances in protein structure prediction and engineering design have made it possible to design new capsid proteins having no sequence homology with existing proteins, but creating the same oligomeric assembly, whether as an individual protein or as a two-component system (Bale et al., 2016). Such engineered proteins with the same similar topological features and the advantageous disposition of the n and/or c-termini for the fusion of proteins or peptides, would be considered within the scope of the invention as set forth below.

Although structurally unique (for example, there are no similarities in the three-dimensional topology of the individual NSP10 proteins with ferritin), they, like members of the ferritin family, are formed by the self-assembling monomeric units. There are no also amino acid sequence homologies between NSPL proteins and the ferritins. While the family of proteins as thus far described are zinc finger proteins, excess zinc is not required for the dodecahedron formation and assembly. Zinc, however, may be required for viral gene regulatory function (Su et al, 2006). The NSPL family of dodecahedrons are similar in size to the smaller dodecameric ferritin capsids induced by heat-shock (which also have nucleic acid binding ability, a property suggested to be protective association (stabilizing) functions). In dodecameric form (12 mer), they are approximately 84 Å in diameter vs. the 100 to 120 Å in diameter for normal 24 mer ferritins with 432 symmetry). In addition to the 12 mer assembly, there is a propensity for these to form dimers as discovered by the crystal structure. Surface electrostatic mapping reveals that the outer shell has definitive patches of positive charge (FIG. 4.) supportive of the proposed role in RNA regulatory processes (Su et al, 2006). Other distinctive features include a predominantly hydrophobic core structure (inner diameter of 36 Å) and examination of the structure space-filling model reveals a series of solvent assessable pores leading from the surface to the interior hollow core.

As previously described, ferritin nanoparticles possess an n-terminus that is located on the capsid surface making possible the display of peptide or protein fusions on the surface creating a VLP display. The types of surface display fusions are limited in this platform to the n-terminus, meaning that the fusion peptide or protein must be fused through the c-terminus of the fusion partner. This is referred to as an N to C terminal fusion requirement. The n-terminus is also located in close proximity to a capsid three-fold axis, making it possible to fuse and display natural oligomeric receptors which require three-fold symmetry. The c-termini of ferritin are located within the interior of the assembled capsid and very closely disposed around a four-fold axis. The c-termini are thus advantageously positioned to fuse peptides or proteins for interior modifications, such as changing the metal affinity and storage properties of ferritin (Kramer, et al, 2004). The c-termini, however are not advantageous in the surface display or the C to N terminal fusion required for a variety of other viral and receptor oligomeric structure requiring surface display and trimeric assembly. Examples of viral receptors that extend from the N to the C-terminus (Influenza, HIV, Ebola and coronaviruses) while other viruses have evolved receptor complexes which extend from the surface with a C to N terminus polarity (such as the reovirus and adenovirus families). Such viral receptors are the most important immunization targets and are key in eliciting neutralizing antibodies that prevent viral infection by blocking the viral receptor interaction and/or conformational requirements for subsequent membrane fusion. Information regarding the ferritin fusion proteins described above is shown in U.S. Pat. Nos. 7,097,841 and 7,608,268, both of these patents and their disclosures incorporated herein by reference.

When characterizing the NSP10 and the subsequent x-ray structure determination, Su et al. (2006) utilize a glutathione-S-transferase (GST) fusion protein for the affinity-based isolation, using a commercially available expression vector with the GST and a specialized protease cleavage site to remove the target protein from the GST. In this way the GST component remains bound to the column and the target protein is easily eluted with relatively high purity. In this manner, Su et al. obtained NSP10 material suitable for further characterization and crystallization. Consequently Su et al. did not evaluate the potential assembly of the GST fusion protein by itself.

As part of the work to evaluate the potential of the NSP10 family of proteins for capsid fusion applications it was necessary to examine the proteins with the fusion partners intact, something that was not demonstrated or suggested by Su et. al., nor since that time, anywhere in the literature. Here, we describe the utility of NSP10 proteins as identified above for a variety of nanoparticle fusion protein applications, and demonstrate for the first time the propensity for self-assembly and proper biological function of the fusion partners once assembled in the capsid form (Examples 1-6). By self-assembly is meant the ability of the protein when formed to fully or partially assemble into the established oligomeric structure including all folds, core regions, pores, and bonding. Self-assembly can also refer to the formation of an aggregate including the proteins of the fusion protein.

Unlike ferritin where the N and C-termini terminate on the exterior and interior of the capsid, respectively, the N and C-termini of NSP10 proteins both are perfectly disposed about the three-fold axes and both terminate on the capsid surface, thus providing a major advantage over prior art. This eliminates the polarity issue, previously described, which limits surface expression partners in ferritin. Most importantly, the termini of each are properly disposed about three-folds with inherent ideal spacing for the fusion of the receptor stems, either helical or fibrous in nature. This positioning creates an anchor point for nucleating the trimeric oligomeric structures of numerous and complex, viral and cellular receptors. The employment of three-fold symmetry created by a fusion partner is well known to catalyze or nucleate the correct folding of a trimeric component (Papanikolopoulou, et al., 2004). Accordingly, the NSP10 proteins of the present invention will be able to be used in the same applications as described above for ferritin, but with the advantages as discussed herein.

As such, these protein or peptide fusions can be used to advantageously display the native form of various viral receptors for a more natural, improved antigen display or to guide the nanoparticle to a therapeutic target. Numerous virus families utilize the three-fold display of stems and receptors, these include the viruses of HIV, Ebola, influenza, coronaviruses, like SARS, MERS, and many others, some of which, like the orbiviruses, do not have an integral stem section, yet still utilize three-fold symmetry of the receptor/host recognition. This receptor display application of the NSP10 agents of the present invention agents can extend beyond viruses into cell tropism of many other infectious diseases and applications, including the targeted delivery of small molecule or protein therapeutic agents to cancerous cells or infectious agents, such as mycobacterial tuberculosis, and parasites, such as malaria. Clearly the scope of the possible applications of the novel NSP10 technology of the present invention is very broad and in addition to the applications described above, including those for the ferritin fusion protein, includes, for example, cell sorting, imaging, material science, vaccines, biosensors, diagnostics, and therapeutics, as described further below.

In this case, the assembled nanoparticle creates two unique sets of four identical three-fold related peptide terminal sequences, namely one set which terminates at the c-terminus and the other set which terminates at the n-terminus where the trimeric sets are each oriented in independent tetrahedral spatial configurations. As a conceptual and visual aide, since the NSP10 proteins of the invention have the same symmetry as a trigonal pyramid, each apex of the pyramid could be thought of as one terminal axis at the three-fold such as the three n-termini, while the c-termini three-folds can be represented by the center of each face of the pyramid (red or blue, see FIG. 7). A further graphic illustrates the final assembly of a c-terminal fusion with a viral stem and receptor (FIG. 8).

Further, an additional set of 4 stem fusions can be constructed on the same particle with the remaining 4 sets of trimeric N termini. FIG. 8 also illustrates the lack of steric spatial restrictions for these fusions, including the large GST fusion tags used for affinity chromatography.

SUMMARY OF THE INVENTION

In conjunction with the present invention, a fusion protein is provided which comprises a self-assembling gene-regulatory NSP10 protein as described above and a protein or peptide capable of being fused to NSP10 without interfering with the assembly or aggregation of the resulting fusion protein. By self-assembling, it is indicated that the fusion protein that forms may be a polymer aggregate, and the self-assembly can be partial or full. The fusion protein of the present disclosure may also be formed into a capsid assembly, such as a dodecameric capsid exhibiting 32 point symmetry. The fusion protein may be formed recombinantly or in a number of suitable chemical or physical ways that would be well known to one skilled in the art. The fusion protein may also have the protein or peptide fused to NSP10 at the n or c-termini positioned at the surface of the NSP10.

Fusion proteins in accordance with the invention may involve fusion of NSP10 with a variety of materials that can be fused to NSP10 without affecting the self-assembly of the protein. The fused material may be a number of suitable peptides or proteins such as antigens, antibodies, viral proteins, fragments or peptides, bacterial proteins, fragments or peptides or virus-like particles (VLP). A number of specific peptides or proteins may be used, including proteins or fragments thereof from an HIV gp120, a coronavirus S gene, HIV gp120, an Influenza hemagglutinin, proteins from an Ebola virus, a MERS virus, a SARS virus, a Zika virus, Dengue fever virus, yellow fever virus, or fragments of proteins thereof. Still further, as set forth below, the NSP10 protein may be assembled so that a material such as a small therapeutic molecule or payload is contained within its hydrophobic core.

The fusion proteins of the invention may also be used as vaccines and/or to enhance immunogenicity of other materials such as antigens and may include use as adjuvants. Such vaccines include anti-parasitic vaccines, anti-insect vaccines, ant-microbial vaccines, anti-protazoan vaccines, cancer vaccines and viral vaccines. The fusion proteins of the invention may also include NSP10 proteins wherein an internalized imaging agent wherein the agent is situated within a hydrophobic core of NSP10. The proteins can thus be used in method of imaging agents. Specific fusion proteins of the invention are shown below and have the sequences of SEQ ID NOS: 1-6. Isolated and/or purified nucleic acid sequences coding for the fusion protein described above are also provided.

In accordance with the invention, an NSP10 fusion protein is thus provided which comprises an NSP10 protein as described above which self assembles into a dodecahedron or higher oligomeric protein form having both the n and c-termini positioned at the surface to which peptide and protein fusions can be made, and a peptide or protein that can fuse to said NSP10 without interfering with the assembly or aggregation of the protein. The NSP10 protein of the other invention can also be formed so that another material, such as a therapeutic small molecule, can be contained within the NSP protein, such as in its hydrophobic core, and such proteins can be used for a variety of purposes including therapeutic drug delivery or other process involving targeting of a particular cell or other biological moiety.

Other applications of the present invention include a method of enhancing the immunogenicity of an antigen comprising fusing said antigen to an NSP10 protein, wherein the antigen can fuse to NSP10 without interfering with the assembly or aggregation of the protein. As with the ferritin case described above, the formation of the NSP fusion protein of the invention provides a link with the fused protein or peptide which dramatically increases the size of the antigen display and can extend the half-life of that protein or peptide. This results in greater exposure of the fused protein or peptide so as to make that protein or peptide more immunogenic and raise larger number of antibodies against it. This may be useful in developing vaccines based on the fusion proteins of the invention.

Another application of the invention is in cell sorting. In accordance with an embodiment of the invention, a method of cell sorting is provided which comprises introducing the NSP fusion protein as described above into a cell sorting apparatus for a time sufficient to allow the fusion protein to bond with a specific type of cell, and then sorting cells based on said bonding. In addition, the present invention can be used for imaging a target material, such as by making a fusion protein with an imaging agent, and introducing the above fusion protein having an imaging agent to a medium containing said target material so as to obtain imaging of said target based on bonding between the fusion protein and said target.

In accordance with the present invention, there is also provided (1) a nanoparticle system that incorporates the C-terminal trimeric fusion of display; (2) a nanoparticle system that incorporates the N-terminal trimeric fusion of display; (3) a nanoparticle system that has both capabilities of use. In one embodiment, both N and C-terminal fusions can be displayed simultaneously on the surface of the same particle.

The present invention also has the added advantage of the tetrahedral arrangement of the expressed proteins allowing for larger fusion partners by reducing the likelihood of steric restrictions created by large fusion proteins caused by the smaller surface area of the nanoparticle. Simultaneous fusions also add the advantage of affinity tags located at the terminus opposite the fusion partner. For example, a protein fused to the N-terminus can also have a c-terminal fusion protein such as GST or a His Tag peptide for affinity-based purifications, without interfering target folding and thus creating greater exposure and availability of the purification tag function. It should be understood that other antigens or peptide fusions can also be displayed by fusion with the NSP10 protein as described above with the same advantages in fusion polarities, and in this case there would be 12 n-terminal monomeric peptides or proteins and/or 12 C-terminal monomeric peptides or proteins (total of 24).

The present invention also provides advantages in the field of vaccines and the use of antigens. For example, the cell receptors of innumerable viruses and other pathogens are invariably formed by trimer oligomerization, as are in turn the cell surface receptors that they recognize. These receptors are responsible for viral cell tropism, with a specialized affinity for specific cells such as lung, intestine, liver, etc. The amino acid sequence polarity of these cells stemming from the viral surface to the cellular receptor can proceed in either the N to C direction or C to N direction, which determines how and on what type of fusion partner they can be associated with.

In this regard, reoviruses and adenoviruses used in the NSP10 fusion proteins of the present invention are perfect examples of a C to N-terminal fusion requirement (for example, the c-terminus of the nanoparticle can be fused to the n-terminus of the fusion partner (antigen)). Ferritin, where the N-terminus is fortuitously located with a three-fold disposition on the exterior of the capsid, does not allow a direct fusion of a natural reoviral stem and receptor (Sigma C) at the three-fold as a single contiguous sequence with the native polarity. However, in the case of the NSP10 proteins of the present invention, both termini are surprisingly set up for fusions at either terminus. Accordingly, a direct fusion of, for example, the Sigma C protein would be made by fusion of the c-terminal residue through appropriate spacing residues, if any, to the n-terminus of the Sigma C viral protein (see Example 4.). The distances between these termini (for example at the n-terminus: ~16.8 Å or ~20.4 Å between C-termini at the capsid three-fold axes) are ideal for fusion to either a fibrous stem as those found in reoviruses or via a helical coiled coil as in influenza or ebola virus. It would be understood that the use of the different terminal fusion types would be an advantage in the creation of multivalent vaccines and other multifunctional nanoparticles.

Another exemplary application of the present invention involving the special antigen display properties of the NSP10 proteins as described above is the ability to apply the dual use of the virus-like particles (VLP) to function together with the receptor targeting, either by antibody-directed attachment or natural receptor fusion. This dual approach, coined "VLP-induced Immune Targeting" (VIT) by the present inventor, made practical by the present invention, can be used to attach a VLP (in this case what is meant is an NSP10 fusion protein) displaying a highly immunogenic antigen, to the surface of the desired target, such as a cancer cell or any other agents, such as immune-evading microbes or parasites. The display of the antigen on the VLP attached to the cell surface of the target signals the destruction of the cell by the immune system. It can also be used as a research tool to selectively destroy subpopulations of cells, or therapeutically to reduce the function of aberrantly active cells. These can be antigens or any of several immune regulatory proteins of interest.

Such an approach can potentially be used for progressive degradation of solid body tumors, and is less likely to induce undesirable autoimmune side effects created by a vaccine that induces antigenicity of a natural protein on the surface of a cancer cell. This information suggests that many serious side effects of vaccines, such as those found with the current live attenuated viruses for yellow fever, may be created by "Virus-Induced Immune Targeting" (VIT), in other words the destruction of the neurological tissue may be created by an active infection of the virus, rather than erroneously labeled as autoimmune disease. Many chronically debilitating diseases labeled as auto-immune could perhaps be the result of VIT (e.g., Guillain-Barre Syndrome, Myasthenia gravis, MS, Parkinson's, Lou Gehrig's disease, and others may include cases where a latent virus, originally held in check by the immune system—an example of latent virus re-emerging in an immune depressed or aging person is Shingles). Another case in point—the extensively used MMR vaccine used in children throughout the United States has been associated with severe and permanent neurological side effects in some children including paralysis and blindness. MMR is a cocktail of three live attenuated viruses. The most popularized theory is that the dangerous side effects produced by MMR are due to the mercurial agent, Thimerosal, used as an antimicrobial and preservative. The principal of VIT suggests two important conclusions, namely that (1) the side effects of at least the two mentioned vaccines can be prevented by a killed virus or recombinant vaccine (including DNA); and (2) where in many of these cases the damage is cyclic, gradual and irreversible over time, this suggests the proper treatment or therapeutics for some of these diseases should include anti-virals against the suspected virus, and these may be provided by the present invention.

BRIEF DESCRIPTION OF THE FIGURES

FIG. 14 (A) shows the SDS PAGE of the GST fusion isolated NSP-IMP fusion protein showing the high relative purity and the significant yield of native material produced by *E. coli* expression. FIG. 14(B) shows native PAGE of the sample shown in "A": Lane 1: protein standard ferritin monomer (~500 kd) and dimer (~1000 kd); Lane 2 NSP-IMP showing two dominant oligomeric forms, one of approximate 300 kd and the other of approximate 600-700 kd.

FIG. 15. The fusion as set forth in Example 6 herein was successfully expressed in both *E coli* and *Bacillus*.

DETAILED DESCRIPTION OF EXEMPLARY EMBODIMENTS

In conjunction with the present invention, a fusion protein is provided which comprises a self-assembling gene-regulatory NSP10 protein as described above which can be utilized as a fusion protein including the NSP10 protein and a protein or peptide capable of being fused to NSP10 without interfering with the assembly or aggregation of the resulting fusion protein. In addition, the fusion protein may comprise the NSP protein with a small molecule or other therapeutic material which may be contained within a hollow interior hydrophobic core of the NSP protein. These fusion proteins may be made in a variety of ways as set forth below, so as these methods allow the protein to undergo self-assembly of the protein form. By self-assembling, it is indicated that the fusion protein that forms may be a polymer aggregate, and the self-assembly can be partial or full. The fusion protein of the present disclosure may also be formed into a capsid assembly, such as a dodecameric capsid exhibiting 32 point symmetry. The fusion protein may be formed recombinantly or in a number of suitable chemical or physical ways that would be well known to one skilled in the art. The fusion protein may also have the protein or peptide fused to NSP10 at the n or c-termini positioned at the surface of the NSP10.

Figure 1:
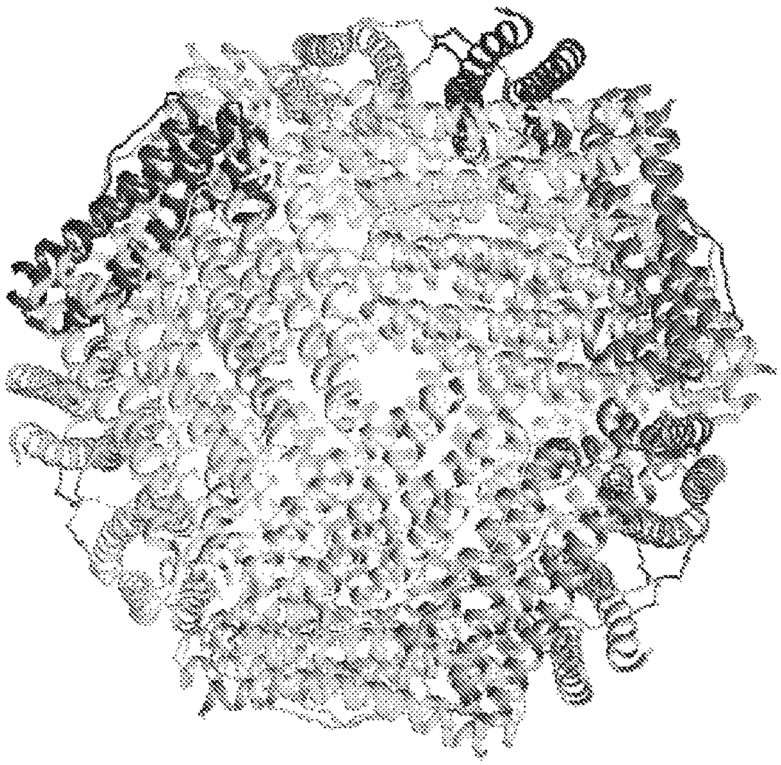
FIG. 1. Each ferritin protein (subunit) shown in separate colors above is comprised of five principal helices (A, B, C, D & E). The N terminus (located on the A helix) and C terminus (located on the E helix) of each 17 kilo Dalton subunit, terminate in the completed quaternary structure on the outer surface and inner core respectively. A typical 24 subunit ferritin will have a diameter of 120 Å and a hollow 80 Å diameter core.
Figure 2:
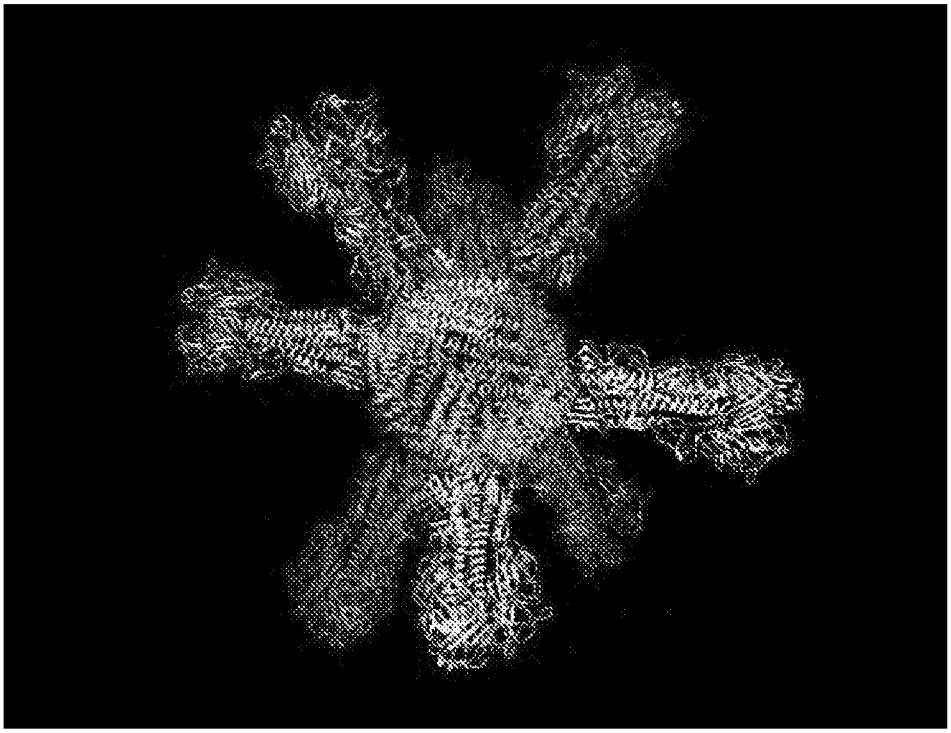
FIG. 2. A graphical image of an example of a ferritin fusion at the 3-fold axes with an influenza hemagglutinin. Individual hemagglutinins and ferritin monomeric units are individually colored.
Figure 3:
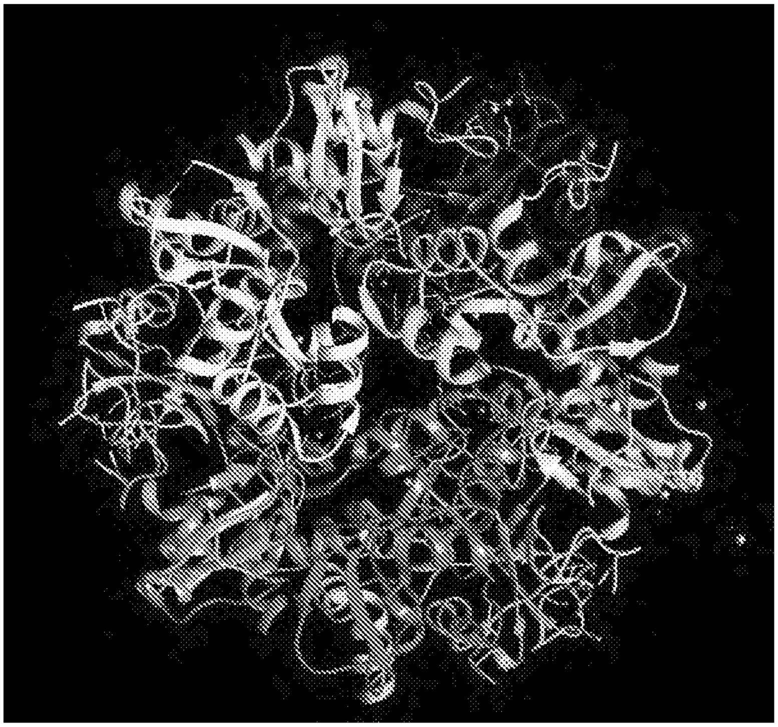
FIG. 3. NSP10 Dodecamer/dodecahedron Viewed down the three-fold showing the close association of the three n-terminal helices. The surface directly opposite has the three c-termini surrounding the three-fold.
Figure 4:
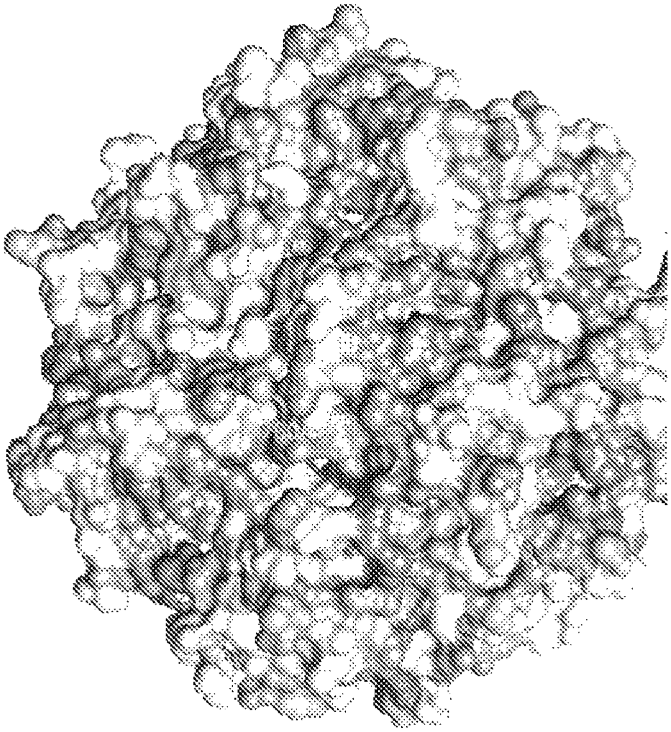
FIG. 4. A space filling surface rendering of the NSP10 capsid illustrating the patches of positive electrostatic charge (shown in blue) on the capsid surface. An individual capsid is approximately ~80 Å in diameter with a hollow ~30 Å hydrophobic core.
Figure 5:
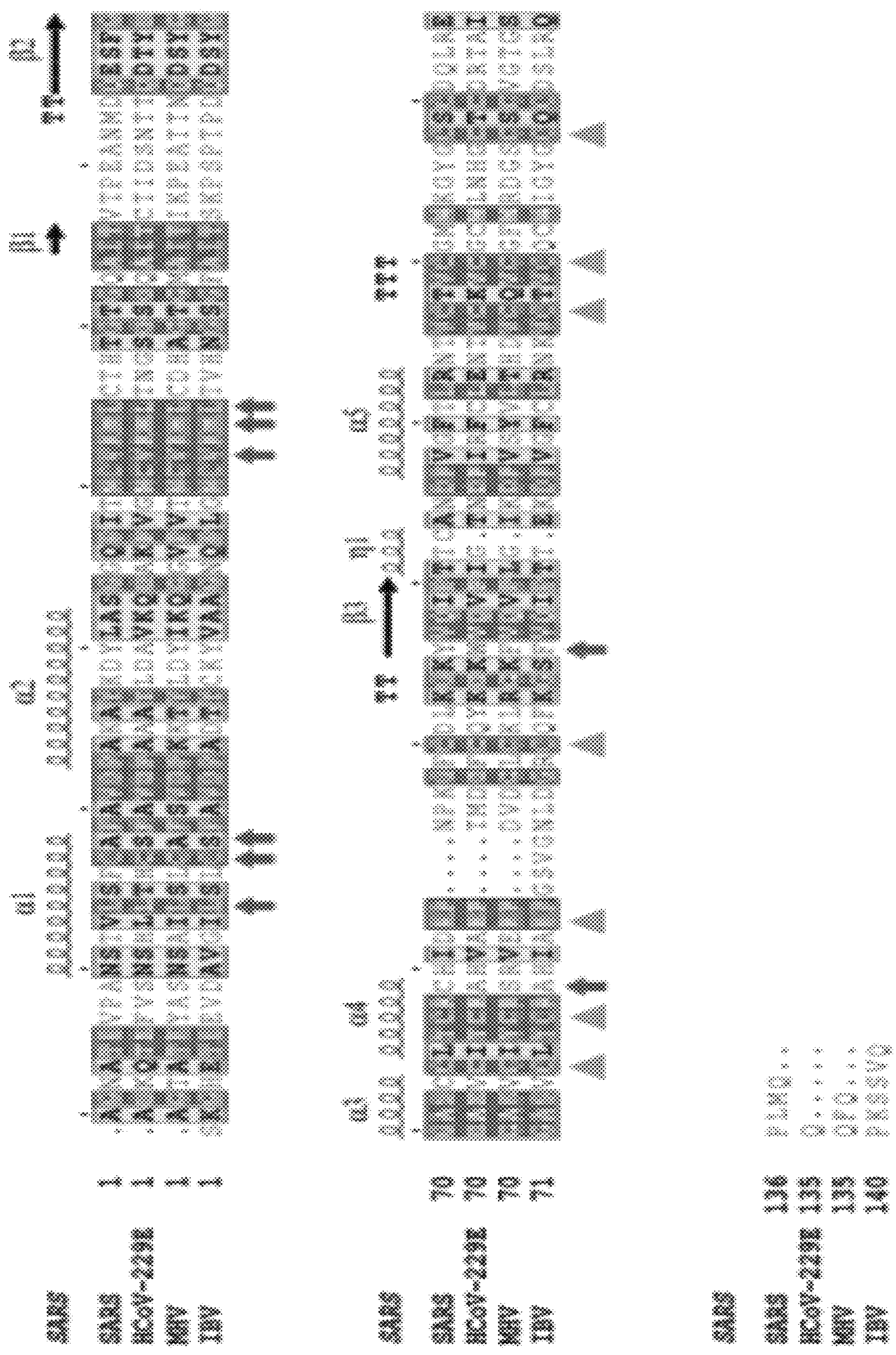
FIG. 5. Illustration from FIG. 5 of reference (1): the sequence homology among the coronavirus NSP-10 family members which suggests a common topology and identical self-assembling dodecahedron structure.
Figure 6:
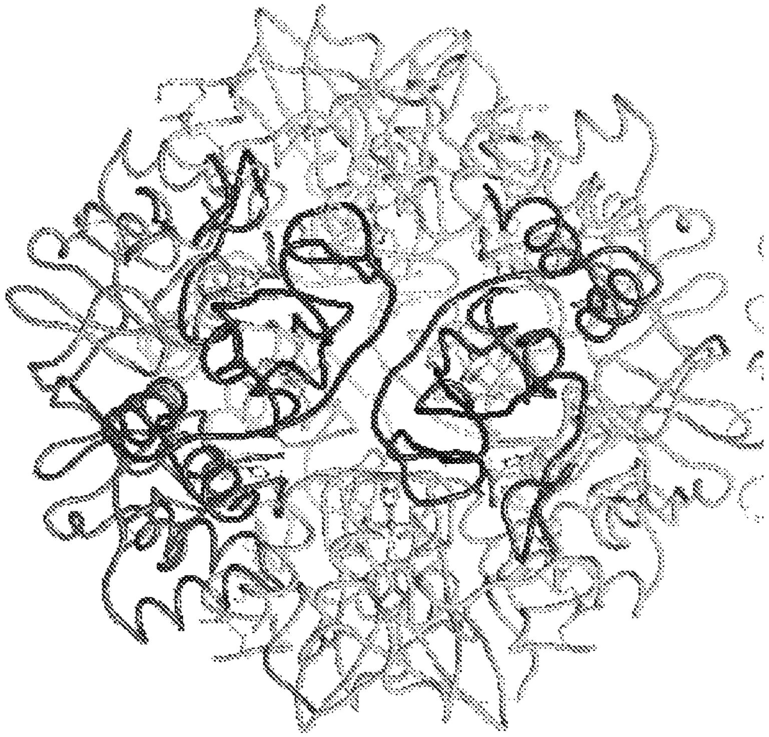
FIG. 6. A view of the NSP10 capsid looking down the two-fold axis. Note the prominent antiparallel beta sheet top surface shown in blue.
Figure 7:
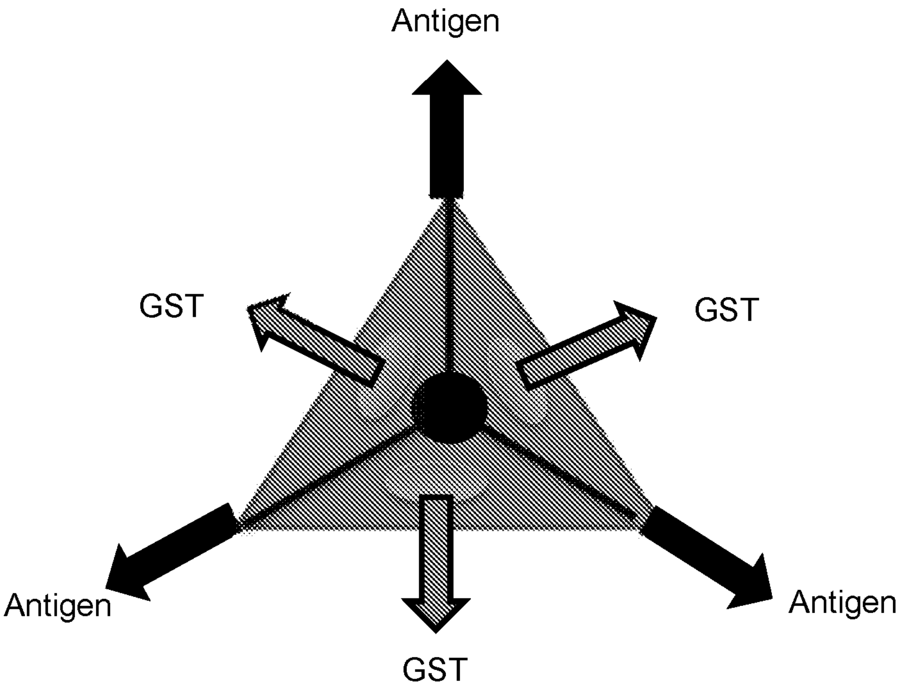
FIG. 7. The trigonal pyramidal structure illustrates the capsid symmetry. The apex of each corner of the trigonal pyramid represents the tetrahedral 3-dimensional arrangement of three-fold axes and the position of one group of the amino acid termini (N or C). For example, arrows denote an antigen display. The position of each three fold axis is indicated by colored arrows. Different colors represent the n or c terminal regions and the tetrahedral arrangement of the capsid three-fold axes. Each three-fold penetrates the capsid, three-fold surfaces on each axis are non-identical (c or n-terminal three-fold axes).
Figure 8:
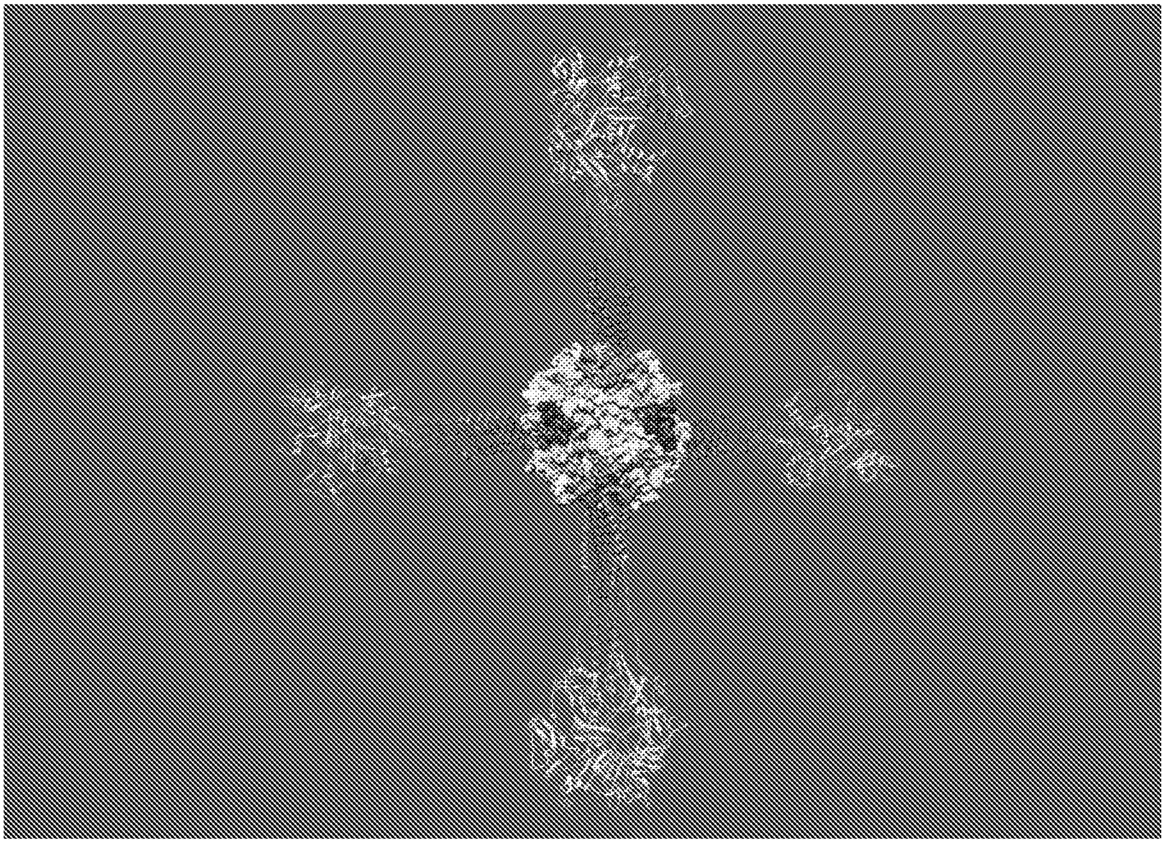
FIG. 8. A graphical depiction of an NSP fusion with a viral stem and receptor. In the example the receptor sequence is fused through the C to N fusion creating 4 spikes which are tetrahedral in arrangement. The remaining visible NSP N-terminal three-fold axes in this orientation, are colored in blue. Note the Sigma C receptor is depicted as a ribbon diagram and the capsid is depicted as a space filling/surface rendering for clarity. Note the significant and unrestricted access to the N-terminal fusion area, shown in blue.
Figure 9:
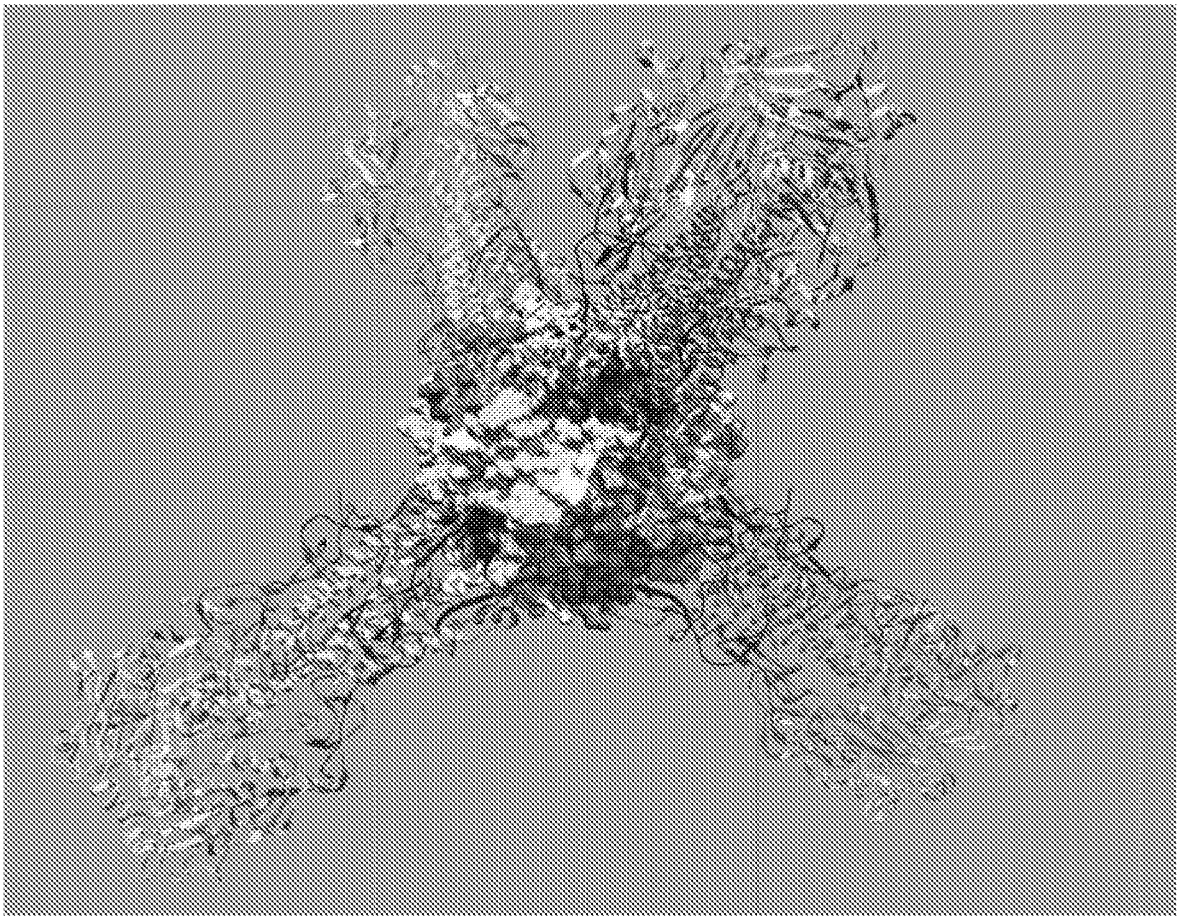
FIG. 9. An atomic model of an influenza hemagglutinin viral receptor and stem illustrating a fusion through the n-terminus of an NSPL capsid and the tetrahedral arrangement of the receptors. Note the hemagglutinin receptor is depicted as a ribbon diagram and the capsid is depicted as a space filling/surface rendering for clarity. Note that even with a large fusion protein, there remains a significant and unrestricted access to the C-terminal fusion area of NSP10, shown in red.
Figure 10:
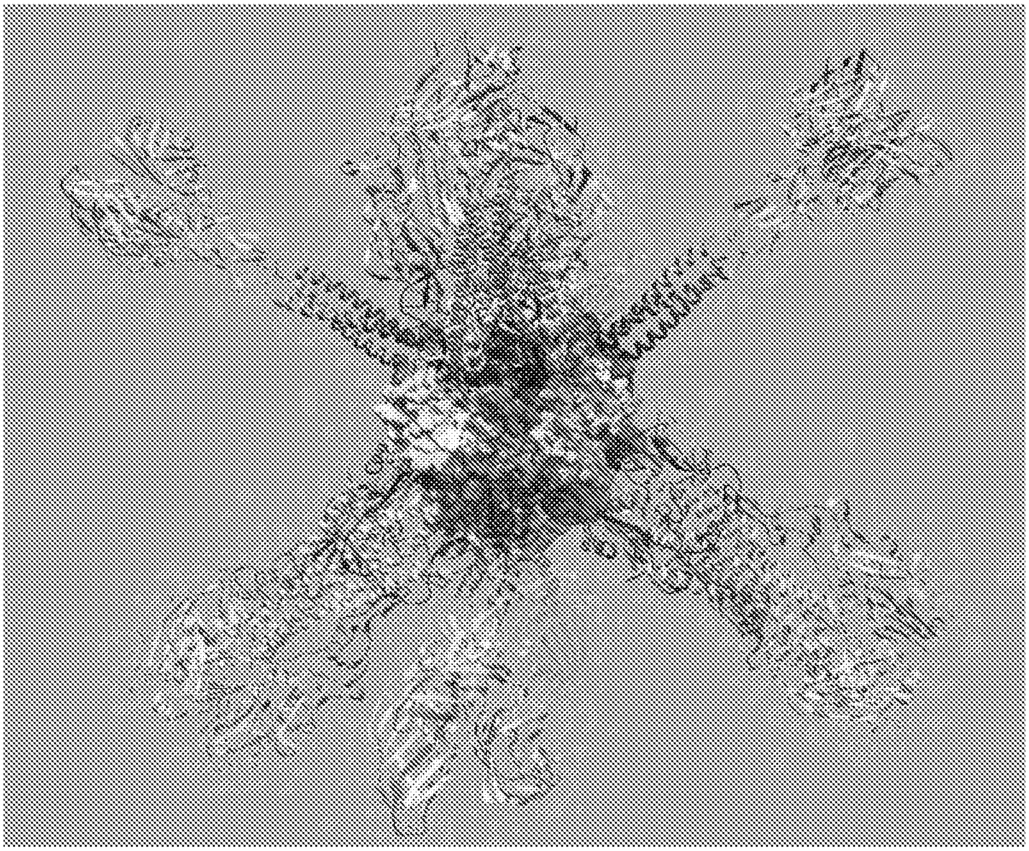
FIG. 10. An atomic model illustrating the combination fusions at both the c and n-termini of NSP10 (Sigma C and hemagglutinin). The receptors are depicted as a ribbon diagram and the capsid is depicted as a space filling/surface rendering for clarity. Note the absence of steric clashes even with the combination of large protein fusions.
Figure 11:
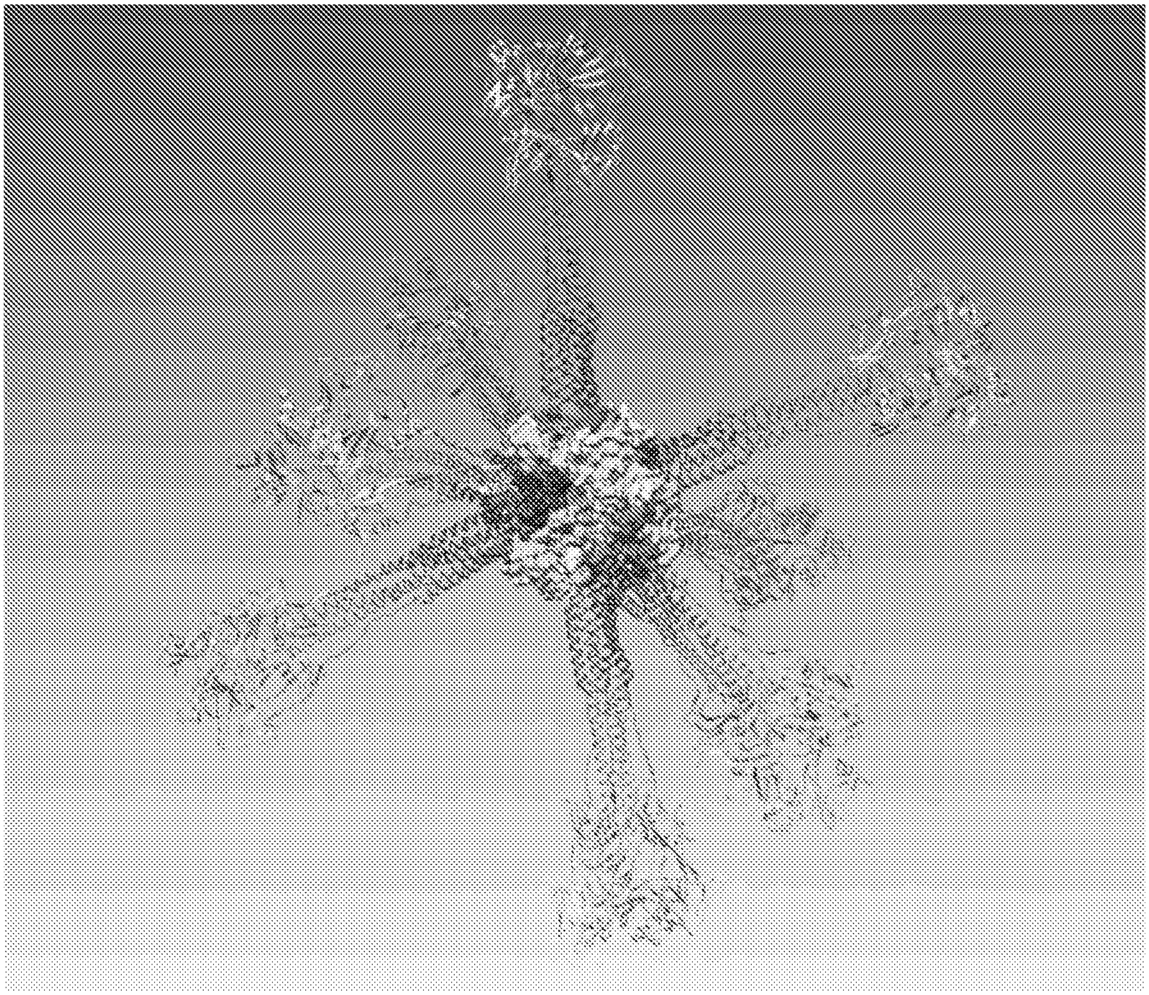
FIG. 11. An atomic model illustrating the application of presenting the same viral stem system from the same family of viruses fused through both termini to create an octamer arrangement. The receptor example shown is from a paramyxovirus where the fusions through the n or c-termini can be designed to utilize the n-terminal helices or modified c-terminal fusion core.
Figure 12:
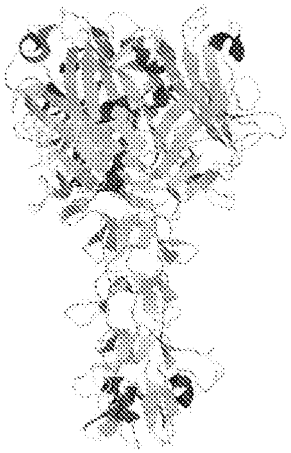
FIG. 12. (A) An example of an adenovirus tri-fold stem and receptor with C to N terminus fusion requirement and (B) the corresponding primary amino acid sequence with observed secondary structure (SEQ ID NO: 9).
Figure 12:
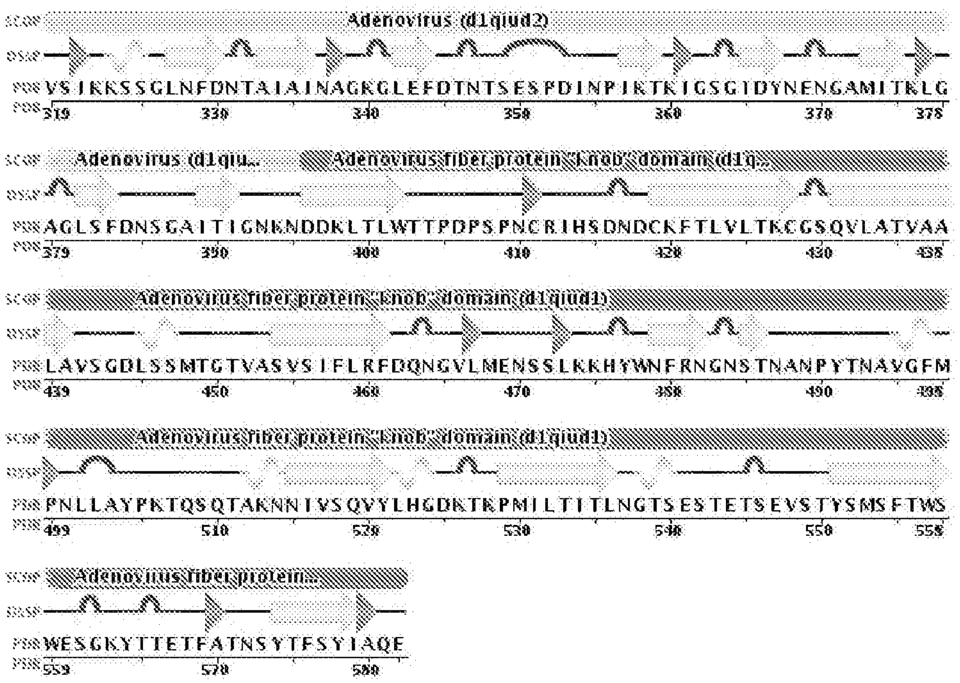

As indicated above, the NSP10 protein of the present invention may have SEQ ID NO:7, or certain sequence homologies thereof, or can also be other proteins that have the same topology or folding pattern of the NSP10 molecule and thus have the same assembly properties as NSP10. In particular, NSP10 self-assembles into a spherical dodecamer having trigonal 32 point symmetry with an outer diameter of approximately 84 Å and an inner hollow hydrophobic chamber of 36 Å in diameter (FIGS. 3 & 4) (see Su et al., 2006; PDB identifier: 2G9T, sequence identifier P0C6U8). The folding topology of NSP10 is a mixed alpha helical and beta sheet structure which can be further described as having two pseudo-subdomains, a small alpha-helical bundle, we denote as subdomain I (residues and helical regions 1-39; 70-91; 104-115) and a small beta sheet domain, we denote as subdomain II (residues 40-70; 90-105). The helical subdomains I self-associate to form a trimer interaction at the four capsid n-terminal three-fold axes and subdomains II self-associate as trimeric units on the four c-terminal three-fold axes. One zinc binding site occurs at the interface between the two subdomains and the three other zinc sites are located within subdomain II near the c-terminus. Accordingly, any protein containing the same folding topology as NSP10 is meant to be encompassed by the NSP10 proteins as described herein. Further, the NSP10 fusion protein can be further stabilized by adding intermolecular cross-linking disulfide bridges so as to reduce or eliminate the zinc binding features of the self-assembly.

The NSP fusion protein as described above may be configured so that the peptide or protein fused to the NSP10 at the n or c-termini positioned at the surface of the NSP10. In addition, the present fusion protein may also be configured wherein the NSP10 has an n-terminus and a c-terminus, and wherein at least one of the two termini are positioned at the surface so as to become available for peptide or protein fusion. The peptide or protein fused to the NSP10 (via recombinant or other means) can be any suitable protein or peptide which can be fused to NSP10 without affecting the self-assembly and/or folding of the molecule as described above.

Accordingly, the peptide or protein fused to NSP10 can be any of a large variety of useful biomolecules, including antigens, viral proteins, fragments, or peptides, bacterial proteins, fragments or peptides, microbial proteins, peptides or fragments, or virus-like particles (VLP). Specific peptides or proteins are discussed below, including proteins or fragments thereof from an HIV gp120, a coronavirus S gene, HIV gp120, an an Influenza hemagglutinin, proteins from an Ebola virus, a MERS virus, a SARS virus, a Zika virus, Dengue fever virus, yellow fever virus, or fragments of proteins thereof. The viral protein, fragment, or peptide may be selected from a wide variety of virus families, including but not limited to Poxviridae, Asfariviridae, Iridoviridae, Herpeseviridae, Baculoviridae, Adenoviridae, Polyomaviridae, Papillomaviridae, Parvoviridae, Reoviridea, Birnaviridae, Coronavridae, Arteriviridea, Togaviridae, Flaviviridae, Picornaviridae, Astroviridea, Caliciviridae, Paramyxoviridae, Filiviridae, Rhabdoviridae, Bornaviridae, Orthomyxoviridae, Bunyaviridae, Arenaviridae, Retroviridae, Hepadnaviridae, and Caulimoviridae.

In the present invention, one application of the fusion protein described herein is as a vaccine composition, or in a method of enhancing immunogenicity or generating antibodies. In one exemplary embodiment, a vaccine may be formed by the fusion protein of NSP10 with a suitable antigen. Vaccine compositions may also be formed from this fusion protein and may include ingredients well known for use in injectable or otherwise administrable vaccines, include conventional vehicles, carriers or excipients that would be well known in the art. The vaccines can be utilized against a wide variety of pathogenic conditions, and may constitute, e.g., anti-parasitic vaccines, anti-insect vaccines, anti-microbial vaccines, anti-protazoan vaccines, cancer vaccines and/or viral vaccines. For example, immunogenic compositions may be prepare which comprise an immunogenic amount of the fusion protein according to claim 1 and a pharmaceutically acceptable vehicle, carrier, or excipient. A list of potential vaccine targets for the present invention include those responsible for Malaria, Dengue Fever, Chikungunya Yellow fever, Zika Virus, Leishmaniaisis, Chagas, Tick-borne encephalitis, hemmoraggic disease, Japanese encephalitis, Influenza virus, rotavirus, common cold virus, coronaviruses. HIV, Ebola, hoof and mouth disease, polio virus, rhinovirus, semliki forest virus, Herpesvirus, tuberculosis, staphylococcus, viral pneumonia, and hepatitis virus.

The NSP10 protein of the invention may also be fused to a protein or fragment from the Apicoplexan or protozoan family of parasites such as Malaria or Chagas disease. The NSP10 protein may also be fused to a viral protein or fragment from a coronavirus S gene. The NSP10 protein may also be configured where the residues lining the inner core, such as the loop containing residues 80-90, are modified or new amino acids are inserted for new functionality. It may also be used as a diagnostic agent or tool in numerous fields, including medical, pharmaceutical, industrial, and numerous other applications.

A method of eliciting an immunogenic reaction in a human or animal comprising administering to said human or animal an immunologically effective amount of the NSP10 fusion protein as described herein. By reference to "effective amount", whether immunologically, pharmaceutically, or in other contexts, is intended to mean any non-toxic but sufficient amount of the compound, composition or agent that produces the desired prophylactic, immunogenic, therapeutic or other effect. Thus, as one skilled in the art would readily understand, the exact amount of the composition or a particular agent that is required will vary from subject to subject, depending on a number of factors including specific condition treated or diagnosed, and age, general condition, and other factors concerning the subject or the treatment, and any dosing regimen will also be determined to suit the individual and the purpose of the treatment. Accordingly, the "effective amount" of any particular compound, composition or agent will vary based on the particular circumstances, and an appropriate effective amount may be determined in each case of application by one of ordinary skill in the art using only routine experimentation.

In another exemplary embodiment of the present invention, the fusion protein of the invention may include an internalized therapeutic payload wherein the payload is situated within a hollow hydrophobic core of the NSP10. Other suitable small molecules, such as imaging agents or other therapeutic molecules that are sized to fit in the hydrophobic core of NSP10 may also be utilized in conjunction with the invention. In general, the hollow cavity in the inner hydrophobic core of the NSP10 protein has a diameter of roughly about 20 to 40 Angstroms and a volume of roughly about 20,000 to 30,000 $Å^3$, thus generally housing materials having widths of about 40 Angstroms or less. It is possible to utilize the hollow central core to trap therapeutics for targeted therapeutic delivery through antibody or receptor directed fusions. This can be done by adjusting the pH and/or buffer properties to cause disassembly of the capsid. Once disassembled, the capsid can be re-assembled in the presence of a therapeutic agent by adjusting the pH and buffer back to the optimum conditions for re-assembly. Therapeutic or diagnostic agents can range from a small protein to peptides or small molecules such as anticancer agents like doxorubicin, cis-platinum, camptothecin, irinotecan, etc. The capacity of the core is limited by the volume and could contain from dozens of large heterocyclic anticancer or other chemical agents, to up to several hundred (400) for smaller anticancer chemotherapeutic agents, such as cisplatin, carboplatin, oxaliplatin, etc. In addition to trapping chemicals during re-assembly, surface mapping reveals a series of pores on the capsid surface that communicate with the central cavity, which suggests that it should be possible to diffuse small molecular agents into the capsid core by establishing the appropriate concentration gradient.

The present fusion proteins of the invention may also be formed into pharmaceutical compositions comprising the fusion proteins with any of a number of well-known suitable, pharmaceutically acceptable vehicles, carrier or excipients. As would be evident to one skilled in the art, such vehicles, carriers or excipients may be any of a wide variety of physical forms in which the fusion protein may be administered when needed for therapeutic or diagnostic purposes. Such suitable forms may include solvents, coatings, antibacterial and antifungal agents, isotonic and absorption enhancing or delaying agents and the like. By "pharmaceutically acceptable" is generally understood to mean that said forms are substantially compatible with the fusion protein or active ingredient therein and/or other ingredients that may be in the composition and is substantially not deleterious to a patient undergoing treatment thereof. General examples of suitable forms include phosphate buffered saline (PBS) and other biologically acceptable buffers, maltodextrin, magnesium carbonate, magnesium stearate, talc, sugar, lactose, pectin, dextrin, starch, gelatin, tragacanth, cellulose, methylcellulose, silicified microcrystalline cellulose, mannitol, such as mannitol 400, glycolate, such as sodium starch glycolate, carboxymethylcellulose, such as sodium carboxymethylcellulose, a low melting wax, cocoa butter, and the like. Other suitable forms include those materials by which the present composition may be formed as a solution, gel, cream, lotion, ointments, drops, and the like.

These compositions may be administered in any of a wide variety of methods, e.g., parenteral, oral, intranasal, subcutaneous, aerosolized or intravenous administration in a human or animal. Other modes of administration, such as enteral, topical, sublingual, intravenous, subcutaneous, intramuscular, percutaneous, or via inhalation may also be used when so determined by one of ordinary skill in the art. In general, when so desired, such pharmaceutical compositions are administered in effective amounts as described above.

The fusion proteins of the present invention may be isolated or purified by any means conventionally used in the art. In addition, isolated nucleic acid sequences coding for the fusion protein are contemplated by the invention. The NSP proteins of the invention may be prepared in a variety of ways using any suitable means well known in the art, including recombinant, chemical or physical means. Recombinant methods of expressing the proteins are well known and can be carried out readily by those of ordinary skill in the art. Such expression methods may be prokaryotic or eukaryotic processes, with or without additional steps such as glycosylation. Other physical or chemical means for the attachment of the fusion protein to the NSP10 would also be well known in the art of fusing proteins.

In accordance with the invention, the NSP protein as described above may be used as an antigen display system for the production of antibodies or the development of vaccines. The proteins of the invention may also be used to display antibody or affinity directing proteins or peptides at either or both termini. With regard to the display of antigens, presentation of antigens to the immune system, or antigen presentation, such are possible using the NSP proteins of the invention. In typical immunogenic formulations, the use of smaller monomeric proteins or peptides that are combined with adjuvants, such as the well-known immunopotentiator known as Freund's Adjuvant which are mineral oil mixtures that promote a strong immune response to the desired antigen. VLPs, which are much larger than the small monomeric protein or peptides, independently serve as immunopotentiators generating a strong immune response by their presence. By displaying the desired antigen on their surface, this serves to focus or direct the immune response to these antigens. For example, small antigenic peptides present greater challenges in eliciting the desired immune response. By fusing and displaying them on the surface of a VLP, a significant improvement in both titer and type of desired immune response can be gained (Li, Soistman & Carter 2006). As a further refinement in the antigen display, when nanoparticles or VLPs can promote the natural display of more complex oligomeric structures on their surface, such as viral receptors or other receptors this is of tremendous value in creating a neutralizing immune response. NSP10 allows the fusion and display of up to 24 peptides or up to 8 trimeric receptors, and allowing for these fusions in the C—N or N—C polarity, a major improvement over the prior art. In addition, two separate sets of trimeric receptors can be readily created and displayed on the surface. In general, the display of antigens on nanoparticles such as NSP10 can be regarded an "antigen display system" or "antigen presentation system."

As indicated above, the NSP proteins of the invention may be fusion proteins, or may be proteins wherein a self-assembling NSP10 protein is formed with a hollow hydrophobic core, and this core may be used to house a variety of small therapeutic or diagnostic materials that can be situated within this hydrophobic hollow core of NSP10. In addition, the NSP10 fusion protein of the invention may comprise an NSP protein which self assembles into a dodecahedron or higher oligomeric protein form having both the n and c-termini positioned at the surface to which peptide and protein fusions can be made, and a peptide or protein that can fuse to said NSP10 without interfering with the assembly or aggregation of the protein.

Still other exemplary methods and uses of the NSP10 protein as described above are possible. For example, a method of enhancing the immunogenicity of an antigen is provided wherein the antigen is fused to an NSP10 protein, wherein the antigen can fuse to NSP10 without interfering with the assembly or aggregation of the protein. A method of cell sorting is also provided comprising introducing the NSP protein of the invention into a cell sorting apparatus for a time sufficient to allow the fusion protein to bond with a specific type of cell, and then sorting cells based on said bonding. A method of imaging a target material is also provided comprising introducing the above NSP protein having an imaging agent to a medium containing said target material and obtaining imaging of said target based on bonding between the fusion protein and said target.

As indicated herein, numerous uses are contemplated for the NSP proteins as described herein, including as antigen display systems for the production of antibodies or the development of vaccines, in order to display antibody or affinity directing proteins or peptides at either or both termini, or to carry an internalized imaging agent within its hydrophobic core. The NSP10 proteins as described herein may also be used as a peptide or protein display systems for applications in biosensors, or for applications in target directed therapeutics. The NSP10 proteins as described above may be used as an attachment scaffold whereby the peptide, small molecule or protein can be attached to the NSP10 protein by a chemical or physical process. Additionally, the NSP10 fusion protein of the invention may be fused or incorporated with a vaccine or other therapeutic in a DNA segment or expression vector for use as a DNA-based injectable. In addition, it will also be possible to co-express NSP10 in a DNA vaccine to enhance production of the recombinant protein of interest As shown above and in the attached examples, It has been demonstrated here that the NSP10 fusion proteins of the invention can be successfully expressed and self-assembled into polymeric forms including dodecamers or higher (e.g., dimeric forms) structures. Both small and large fusions have been successfully demonstrated as illustrated in the examples. Further, these have been demonstrated in two different prokaryotic systems and one eukaryotic system to date. In cases where the complexity or post translational modifications are desired or required for the proper activity or antigenicity, these systems can also be expressed in systems such as yeast, CHO cells, HK293 cells, insect cells or transgenic plants. The choice of system would be necessitated by the application and thus easily anticipated by one skilled in the art. Accordingly, it would be understood that the expression vectors or GMO viruses could be used directly in animals to express the nanoparticles in vivo for the same purposes outlined herein. Such applications and others would be considered within the scope of this invention.

It is also possible to utilize sterile filtration for NSP10 nanoparticles. Because of the slightly lower micron size as compared with other nanoparticles, these particles are more readily filterable with 0.2 micron filtration to sterilize the final formulation. Sterile formulations with 10% glycerol can be frozen at −80° C. for long term storage.

NSP10 may also be utilized as a host cell protein suppressor. As indicated above, NSP10 is a viral gene regulatory/replicase-inhibitor protein that binds to the host cell 40S ribosomal unit and inhibits translation of host proteins. By suppressing host cell expression, NSP10 facilitates the production of its own viral gene expression. The Co-expressing the NSP-10 family of proteins, by itself or together with other proteins for therapeutic purposes or as a inclusion in a DNA vaccine or therapeutic for the express purpose of suppressing the translation of the host proteins is thus contemplated in the present invention Suppression of host cell proteins by a properly constructed DNA vaccine would ensure a greater amount of the antigen or VLP was produced, lowering the DNA required for effective dose and lowering the cost of production. The Table below shows the sequence of one Nonstructural protein 10 in accordance with the present invention:

TABLE I

| |
|---|
| Nonstructural protein 10, NSP10 (d2g9td1) (SEQ ID NO: 1) |
| AGNATEVPANSTVLSFCAFAVDPAKAYKDYLASGGQPITNCVKMLCTHT |
| GTGQAITVTPEANMDQESFGGASCCLYCRCHIDHPNPKGFCDKGKYVQI |
| PTTCANDPVGFTLRNTVCTVCGMWKGYGCSCDQLREPLMQSADASTLFN |
| GFAV |

The amino acid sequence of NSP-10, the underlined sequence indicates the required amino acids for capsid construction. The core capsid encompasses 122 amino acids (~14 kd), vs 151 total (~17 kd). The underlined sequence itself is shown below:

(SEQ ID NO: 7)
PANSTVLSFCAFAVDPAKAYKDYLASGGQPITNCVKMLCTHTGTGQAIT

VTPEANMDQESFGGASCCLYCRCHIDHPNPKGFCDKGKYVQIPTTCAND

PVGFTLRNTVCTVCGMWKGYGCS

Still further, the present NSP-10 proteins as described herein by be useful in all applications of nanomaterial synthesis and plasmon resonance. With regard to recombinant expression, suitable methods can be employed as described above, and can include transgenic production in plants, (e.g., rice, tobacco, etc.) and animals. The NSP10 proteins can also be used in a number of diagnostic applications as well, including diagnoses relating to disease conditions or other applications involving small molecules, e.g., in the medical, pharmaceutical and industrial fields.

EXAMPLES

Example 1

The sequence of a hemagglutinin H5 fusion protein is shown below with the fusion at the N-terminus of NSP10. In the sequence below, the NSP10 sequence is underlined, and the linking residues are shown in bold.

Hemagglutinin 115 Fusion at N-terminus of NPS10
(SEQ ID NO: 2)
DQICIGYHANNSTKQIDTIMEKNVTVTHAQDILEKKHNGKLCSLKGVKP

LILKDCSVAGWLLGNPMCDEFLNAPEWSYIVEKNNPINGLCYPGDFNDY

EELKHLVSSTNLFEKIRIIPRNSWTNHDASSGVSSACPHLGRSSFFRNV

VWLIKKNNVYPTIKRTYNNTNVEDLLILWGIHHPNDAAEQAKLYQNLNA

YVSVGTSTLNQRSIPKIATRPKVNGQSGRMEFFWTILRPNDTISFESTG

NFIAPEYAYKIVKKGDSAIMRSELEYGNCDTKCQTPLGAINSSMPFHNV

HPLTIGECPKYVKSDKLVLATGMRNVPQKKKRGLFGAIAGFIEGGWQGM

VDGWYGYHHINGQGSGYAADKKSTQKAIDGITNKVNSIIDKIVINTQFE

AVGREFNNLERRIENLNKKMEDGFIDVWTYNAELLVLMENERTLDLHDS

NVKNLYDKVRLQLRDNAKELGNGCFEFYHKCDNEClVIESVRNGTYNYP

KYSESGGSPANSTVLSFCAFAVDPAKAYKDYLASGGQPITNCVKMLCTH

TGTGQAITVTPEANMDQESFGGASCCLYCRCHIDHPNPKGFCDLKGKYV

QIPTTCANDPVGFTLRNTVCTVCGMWKGYGCS (About 617 residues or 83.6 kd)

Example 2

The sequence of a Gp41 component fusion via the N-terminus of NSP10 is shown below. In the sequence below, the NSP10 sequence is underlined, and the linking residues are shown in bold.

Gp41 component Fusion via the N-terminus of NPS10
(SEQ ID NO: 3)
EAIVNAQPKCNPNLHYWTTQDEGAAIGLAWIPYFGPAAEGIYTEGLMEN
QDGLICGLRQLANETTQALQLFLRATTELRTFSILNRKAIDFLLQPANS
TVLSFCAFAVDPAKAYKDYLASGGQPITNCVKMLCTHTGTGQAITVTPE
ANMDQESFGGASCCLYCRCHIDHPNPKGFCDLKGKYVQIPTTCANDPVG
FTLRNTVCTVCGMWKGYGCS Additional Examples of fusions are provided in Examples 3 and 4 below.

Example 3

Reoviral Fibrous Stem and Receptor

Figure 16:
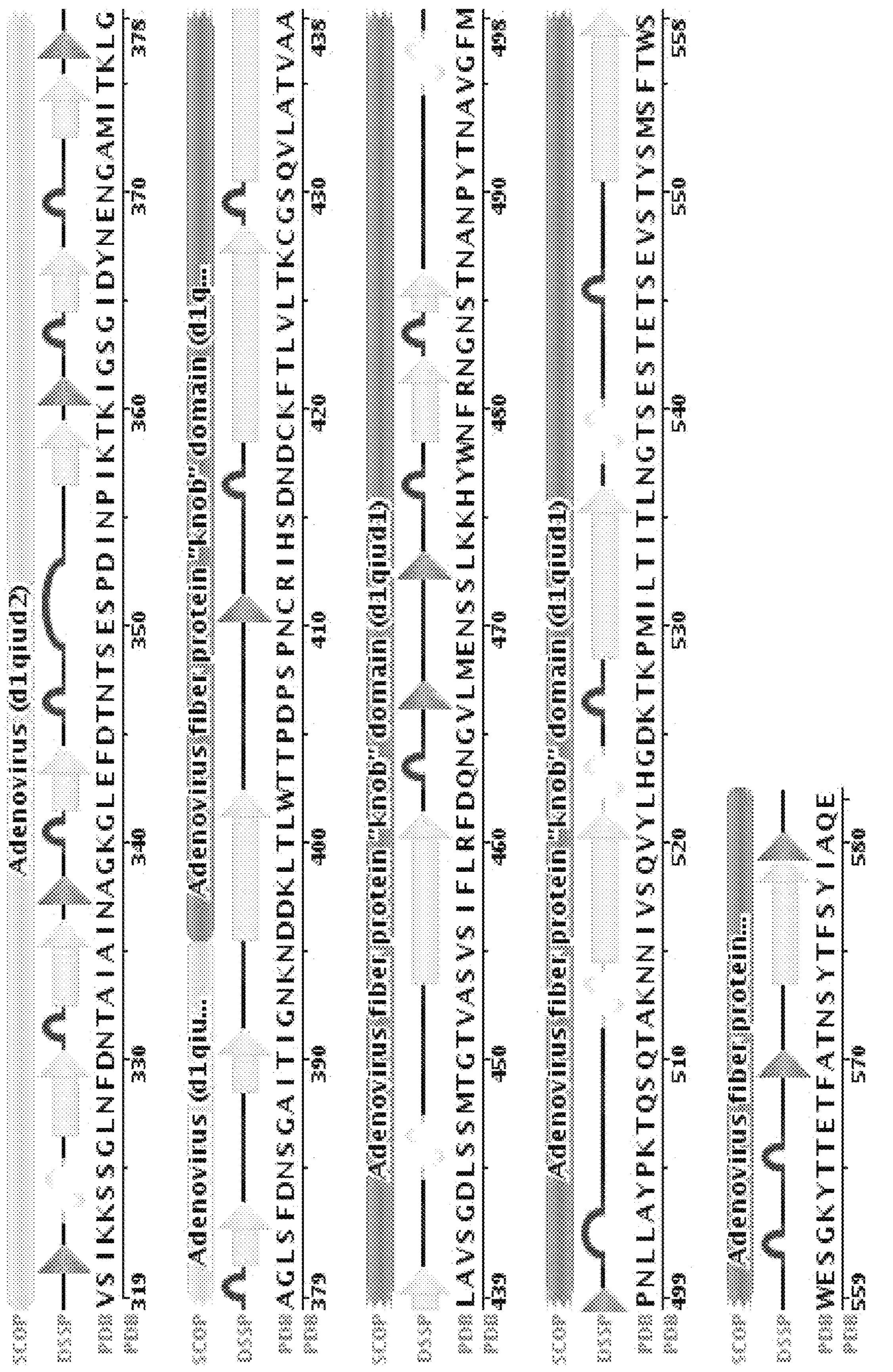
FIG. 16. This figure shows the remainder of the Reoviral Fibrous Stem and Receptor as described in Example 3.

PANSTVLSFCAFAVDPAKAYKDYLASGGQPITNCVK-MLCTHTGTGQAITVTPEA NMDQESFGGASCCLY-CRCHIDHPNPKGFCDLKGKYVQIPTTCANDPVGFTL-RNT VCTVCGMWKGYGCSGGS, with the remainder as shown in FIG. 16.

Example 4

Sigma-C Capsid Protein Fusion OS=Avian Reovirus (Strain S1133) (Including Trimeric Helical Stem)

(SEQ ID NO: 4)
PANSTVLSFCAFAVDPAKAYKDYLASGGQPITNCVKMLCTHTGTGQAIT
VTPEANMDQESFGGASCCLYCRCHIDHPNPKGFCDLKGKYVQIPTTCAN
DPVGFTLRNTVCTVCGMWKGYGCSGGSMAGLNPSQRREVVSLILSLTSN
VNISHGDLTPIYERLTNLEASTELLHRSISDISTTVSNISANLQDMTHT
LDDVTANLDGLRTTVTALQDSVSILSTNVTDLTNRSSAHAAILSSLQTT
VDGNSTAISNLKSDISSNGLAITDLQDRVKSLESTASHGLSFSPPLSVA
DGVVSLDMDPYFCSQRVSLTSYSAEAQLMQFRWMARGTNGSSDTIDMTV
NAHCHGRRTDYMNISSTGNLTVTSNVVLLTFDLSDITHIPSDLARLVPS
AGFQAASFPVDVSFTRDSATHAYQAYGVYSSSRVFTITFPTGGDGTANI
RSLTVRTGIDT 451 residues—about 61 kd

Example 5

Demonstration of Practical Application without Undo Experimentation

NSP-IMP
(SEQ ID NO: 5)
PANSTVLSFCAFAVDPAKAYKDYLASGGQPITNCVKMLCTHTGTGQAIT
VTPEANMDQESFGGASCCLYCRCHIDHPNPKGFCDLKGKYVQIPTTCAN
DPVGFTLRNTVCTVCGMWKGYGCSMGAACGKSQRAAAAVEPPLSTAEKA
EAAAVAAAEHSQKAEEAAEVAAACATKASAEAAVLTGVEPGAEPAAEAE
EAPKQNEIEEQQTTTSPAQTHATEEQPAAPPVVPLSDADAQVLAAAEAA

-continued

KQEAASSNMPRAYLFYACELNEGSLMNIQWTTTQITEEDMHAKNLILLA
SFVPAKHKTVSKSKLTQNGGITYFLQEMKYKWEVWSKVQRQAYYQGWIK
FVKAADEMEASFTLHHFAAPAPPAKLFLLHTGPIENKVLPAKEEEPFNV
SVFGLAAVTPPSPPYKPGANITPKRFGEIATGAGGAYMQLSRRGGDAAF
DEKEVQKWLAADGLQMKKGEGITLDAAGGYERRSEKKGGDAAAATAAVE
AEPTKVSQD

Figure 13:
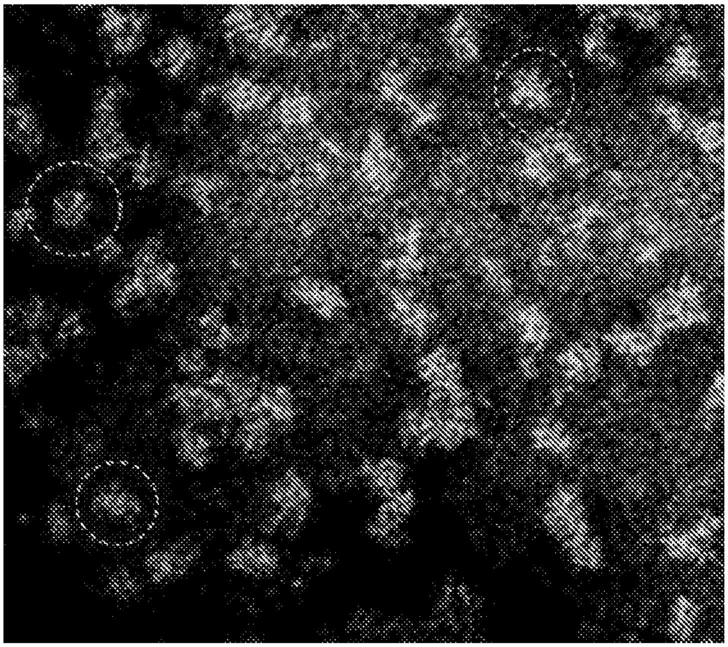
FIG. 13 is a photographic image of a TEM revealing numerous NSPL VLPs of the native IMP fusion material confirming the formation of the large oligomeric structures as indicated by native PAGE electrophoresis.

Expression in bacteria using an expressionvector with a removable GST fusion protein for simplification of purification. Two viral fusion proteins were made through the c terminus, both were clearly expressed and captured by GST or His tag affinity chromatography yielding relatively pure protein. SDS gel electrophoresis of the isolated GST fusion protein were in accordance with the predicted molecular weights and Native PAGE electrophoresis indicated approximately 50% in fully assembled capsid and the remaining 50% in a single band representing a smaller oligomeric form. In the case of His tag expression which had a smaller fusion partner, 100% of the monomeric form was incorporated—self-assembled into the capsid. These gels are shown in FIGS. 14(A) and 14(B), wherein in A, the SDS PAGE of the GST fusion isolated NSP-IMP fusion protein showing the high relative purity and the significant yield of native material produced by *E. coli* expression is provided. In B, the native PAGE of the sample shown in "A" is provided wherein Lane 1 is a protein standard ferritin monomer (~500 kd) and dimer (~1000 kd); and Lane 2 is NSP-IMP showing two dominant oligomeric forms, one of approximate 300 kd and the other of approximate 600-700 kd. A TEM revealing numerous NSPL VLPs of the native IMP fusion material confirming the formation of the large oligomeric structures as indicated by native PAGE electrophoresis is shown in FIG. 13.

Example 6

Demonstration of Practical Application without Undo Experimentation

NSP-EDS
(SEQ ID NO: 6)
PANSTVLSFCAFAVDPAKAYKDYLASGGQPITNCVKMLCTHTGTGQAIT
VTPEANMDQESFGGASCCLYCRCHIDHPNPKGFCDLKGKYVQIPTTCAN
DPVGFTLRNTVCTVCGMWKGYGCSGGGSDGELTLAYDSTDFQVTENGLA
LKVSPTQTPLTRIISMGNNLFDSGYEIFASCPQNKAAKVAGYVYLTSVG
GLVHGTIQIKATAGYWFTGGNSVQESIRFGLVLCPFSARDPTANLSGWP
APVVWSGDSNTPLYFAANAISYTNNRVNLAVTGNFYKEETELPGYTRHS
FCPTGTTGMNFTGGNLYVCPCTVNTGATTLNAIYMVFVITQSALGTNFF
ASNTPPNTFFLTPPIPFTYVGAQ

Figure 14:
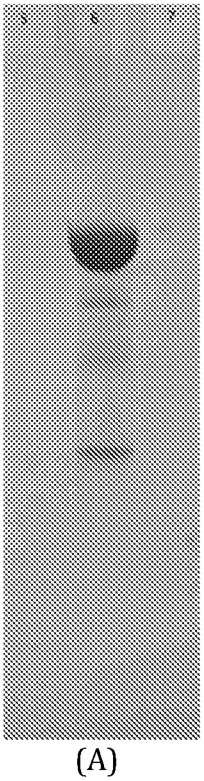
FIG. 14.
Figure 14:
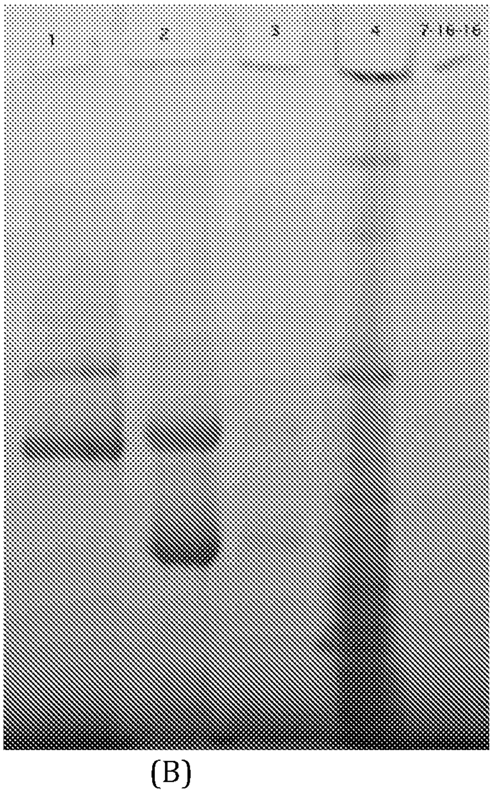
Figure 15A:
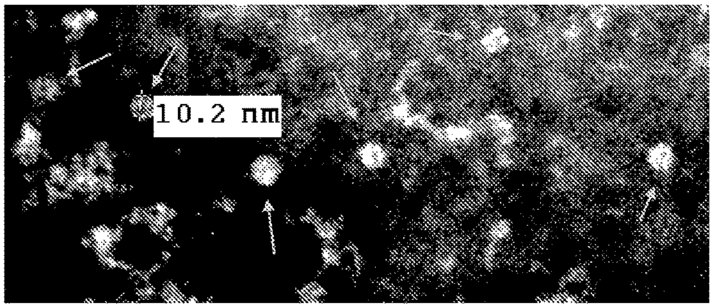
FIG. 15(A) shows the TEM image of the *Bacillus* material as isolated by His tag affinity chromatography and FIG. 15(B) is a demonstration of hemagglutination activity—biological function, of the assembled nanoparticle.
Figure 15B:
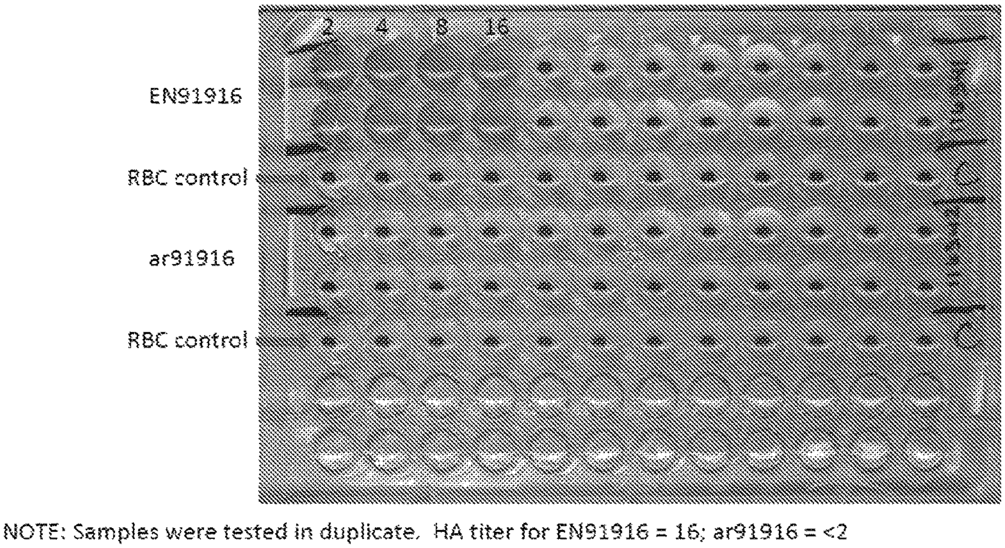

The Fusion protein above was successfully expressed in both *E coli* and *Bacillus*. This is shown in FIG. 14 (A) which is the TEM image of the *Bacillus* material as isolated by His tag affinity chromatography and in FIG. 14(B) which is the demonstration of hemagglutination activity—biological function, of the assembled nanoparticle.

In summary, Described herein is a self-assembling gene regulatory protein NSP-10 which assembles into a dodecameric capsid exhibiting 32 point symmetry. In the assembled capsid the specialized positions of the N and C termini occur at points of 3-fold capsid symmetry properly disposed with the correct distances from the triad to anchor the fusion peptide a t the three-fold and promote nucleation of the correct folding for complex helical or fibrous trimeric assemblies, such as those found on viral receptors responsible for tropism and cell infection. Native formation of these viral receptor assemblies are essential properties of antigens (and vaccines) which prompt the immune system to create highly potent and broadly neutralizing antibodies. Such scaffolds can also serve as points of fusion for cellular receptors for targeting the delivery of therapeutics for cancerous cells or other therapeutically important targets. Here we have shown that complex fusions can be made which overcome protein fusion sequence polarity restrictions that limit the applications of other vaccine nanoparticle display systems. The invention described herein is one of the most unique and versatile nanoparticle fusion systems created to date, allowing for surface displaying fusions from both the c and n-termini. Complex divalent functionalities easily achieved in a single nanoparticle and with advantages in purification and other properties desirable for vaccine, therapeutic or other nanoparticle development.

It will be understood that various details of the presently disclosed subject matter can be changed without departing from the scope of the subject matter disclosed herein. Furthermore, the foregoing description and examples are for the purpose of illustration only, and not for the purpose of limitation.

REFERENCES

The following references which are cited above are incorporated by reference herein as if set forth in their entirety:

Bale et al., "Accurate design of megadalton-scale two-component icosahedral protein complexes," Science 353, 389-394 (2016).

Carter, D. C., Li., C. "Ferritin Fusion Proteins for Use in Vaccines and Other Applications," U.S. Pat. No. 10,435, 666 (2003).

C. Li, E. Soistman and D. C. Carter, "Ferritin Nanoparticle Technology: A New Platform for Antigen Presentation and Vaccine Development," *Industrial Biotechnology*, Vol. 2, No. 2, 143-147 (2006).

Hewakuruppu, Y., et al, "Plasmonic "pump-probe" method to study semi-transparent nanofluids," Applied Optics, 52 (24): 6041-6050 (2013)

Joseph et al., "Crystal structure of nonstructural protein 10 from the severe acute respiratory syndrome coronavirus reveals a novel fold with two zinc-binding motifs." *J Virol* 2006 August; 80(16):7894-901

Kanekiyo et al., "Self-assembling influenza nanoparticle vaccines elicit broadly neutralizing H1N1 antibodies," Nature. 2013 May 22 doi:10.10138/nature.12202).

Kramer, R. M., Li, C., Carter, D. C. Stone, M. O., Naik, R. R., "Engineered Protein Cages for Nanomaterial Synthesis," J. Am. Chem. Soc., Vol. 126, No. 41 (2004). "Once-in-a-Lifetime Flu Shot?" Science Vol 341: pg. 1171, September, 2013

Papanikolopoulou, K., et al., "Adenovirus fibre shaft sequences fold into native triple beta-spiral fold when N-terminally fused to the bacteriophage T4 fibritin foldon trimerisation motif," J. Mol. Biol. (2004) 342:219.

Su, et. al., "Dodecamer structure of Severe Acute Respiratory Syndrome Coronavirus Nonstructural Protein nsp10," J. Virol. August 2006, p 7902-7908.

Wang, Z. et al, "Structure of Human Ferritin L Chain," Acta Cryst., D62, 800-806 (2006).

What is claimed is:

1. A fusion protein comprising a self-assembling coronavirus NSP10 protein and a protein or peptide capable of being fused to NSP10 without interfering with the assembly or aggregation of the resulting fusion protein, wherein the fusion protein forms a capsid assembly, and wherein the capsid is a dodecameric capsid exhibiting 32 point symmetry.

2. The fusion protein according to claim 1 wherein the fusion protein forms a polymer aggregate.

3. The fusion protein of claim 1 wherein the protein or peptide fused to NSP10 is fused at the n or c-termini positioned at the surface of the NSP10.

4. The fusion protein of claim 1 wherein the NSP10 has an n-terminus and a c-terminus, and wherein at least one of the two termini are positioned at the surface so as to become available for peptide or protein fusion.

5. The fusion protein of claim 1 wherein the peptide or protein fused to NSP10 is an antigen.

6. The fusion protein of claim 1 wherein the peptide or protein fused to NSP10 is a viral protein, fragment, or peptide, a bacterial protein, fragment or peptide, a virus-like particle (VLP), an immune regulatory protein, a microbial protein.

7. The fusion protein of claim 4 wherein the peptide or protein fused to NSP10 is selected from the group consisting of hemoglobin, silver condensing peptide, the HIV Tat protein, the small HIV Tat peptide, HIV-1 P24 protein, HIV gp120 proteins or fragments thereof from an HIV gp120, a coronavirus S gene, an Influenza hemagglutinin, proteins from an Ebola virus, a MERS virus, a SARS virus, a Zika virus, Dengue fever virus, yellow fever virus, or fragments of proteins thereof.

8. A vaccine composition comprising the fusion protein of claim 1 and a pharmaceutically acceptable vehicle, carrier, or excipient.

9. The vaccine composition of claim 8 wherein the vaccine is selected from the group consisting of anti-parasitic vaccines, anti-insect vaccines, anti-microbial vaccines, anti-protozoan vaccines, cancer vaccines and viral vaccines.

10. An immunogenic composition comprising an immunogenic amount of the fusion protein according to claim 1 and a pharmaceutically acceptable vehicle, carrier, or excipient.

11. The fusion protein of claim 1 wherein the peptide or protein fused to NSP10 is an internalized therapeutic payload wherein the payload is situated within a hydrophobic core.

12. The fusion protein of claim 1 wherein the peptide or protein fused to NSP10 is an internalized imaging agent wherein the agent is situated within a hydrophobic core of NSP10.

13. A pharmaceutical composition comprising the fusion protein according to claim 1 and a pharmaceutically acceptable vehicle, carrier or excipient.

14. A fusion protein comprising a self-assembling NSP10 protein and a protein or peptide capable of being fused to NSP10 without interfering with the assembly or aggregation of the resulting fusion protein, wherein the NSP10 has the sequence of SEQ ID NO: 7.

15. An isolated nucleic acid sequence coding for the fusion protein according to claim 14.

16. A fusion protein comprising a self-assembling coronavirus NSP10 protein and a protein or peptide capable of being fused to NSP10 without interfering with the assembly or aggregation of the resulting fusion protein, wherein the protein is further stabilized by adding intermolecular cross-linking disulfide bridges or amino acid substitutions so as to reduce or eliminate the zinc binding features of the self-assembly.

17. The fusion protein of claim 6 wherein the peptide or protein fused to NSP10 is a viral protein, fragment, or peptide, and wherein the virus is from a virus family selected from the group consisting of Poxviridae, Asfariviridae, Iridoviridae, Herpeseviridae, Baculoviridae, Adenoviridae, Polyomaviridae, Papillomaviridae, Parvoviridae, Reoviridea, Birnaviridae, Coronavridae, Arteriviridea, Togaviridae, Flaviviridae, Picornaviridae, Astroviridea, Caliciviridae, Paramyxoviridae, Filiviridae, Rhabdoviridae, Bornaviridae, Orthomyxoviridae, Bunyaviridae, Arenaviridae, Retroviridae, Hepadnaviridae, and Caulimoviridae.

* * * * *

SEQUENCE LISTING

```
<160> NUMBER OF SEQ ID NOS: 9

<210> SEQ ID NO 1
<211> LENGTH: 151
<212> TYPE: PRT
<213> ORGANISM: SARS coronavirus

<400> SEQUENCE: 1

Ala Gly Asn Ala Thr Glu Val Pro Ala Asn Ser Thr Val Leu Ser Phe
1               5                   10                  15

Cys Ala Phe Ala Val Asp Pro Ala Lys Ala Tyr Lys Asp Tyr Leu Ala
            20                  25                  30

Ser Gly Gly Gln Pro Ile Thr Asn Cys Val Lys Met Leu Cys Thr His
        35                  40                  45

Thr Gly Thr Gly Gln Ala Ile Thr Val Thr Pro Glu Ala Asn Met Asp
    50                  55                  60

Gln Glu Ser Phe Gly Gly Ala Ser Cys Cys Leu Tyr Cys Arg Cys His
65                  70                  75                  80

Ile Asp His Pro Asn Pro Lys Gly Phe Cys Asp Lys Gly Lys Tyr Val
                85                  90                  95

Gln Ile Pro Thr Thr Cys Ala Asn Asp Pro Val Gly Phe Thr Leu Arg
            100                 105                 110

Asn Thr Val Cys Thr Val Cys Gly Met Trp Lys Gly Tyr Gly Cys Ser
        115                 120                 125
```

```
Cys Asp Gln Leu Arg Glu Pro Leu Met Gln Ser Ala Asp Ala Ser Thr
    130                 135                 140

Leu Phe Asn Gly Phe Ala Val
145                 150


<210> SEQ ID NO 2
<211> LENGTH: 616
<212> TYPE: PRT
<213> ORGANISM: SARS coronavirus

<400> SEQUENCE: 2

Asp Gln Ile Cys Ile Gly Tyr His Ala Asn Asn Ser Thr Lys Gln Ile
1               5                   10                  15

Asp Thr Ile Met Glu Lys Asn Val Thr Val Thr His Ala Gln Asp Ile
            20                  25                  30

Leu Glu Lys Lys His Asn Gly Lys Leu Cys Ser Leu Lys Gly Val Lys
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Ala Pro Glu Trp Ser Tyr Ile Val
65                  70                  75                  80

Glu Lys Asn Asn Pro Ile Asn Gly Leu Cys Tyr Pro Gly Asp Phe Asn
                85                  90                  95

Asp Tyr Glu Glu Leu Lys His Leu Val Ser Ser Thr Asn Leu Phe Glu
            100                 105                 110

Lys Ile Arg Ile Ile Pro Arg Asn Ser Trp Thr Asn His Asp Ala Ser
        115                 120                 125

Ser Gly Val Ser Ser Ala Cys Pro His Leu Gly Arg Ser Ser Phe Phe
    130                 135                 140

Arg Asn Val Val Trp Leu Ile Lys Lys Asn Asn Val Tyr Pro Thr Ile
145                 150                 155                 160

Lys Arg Thr Tyr Asn Asn Thr Asn Val Glu Asp Leu Leu Ile Leu Trp
                165                 170                 175

Gly Ile His His Pro Asn Asp Ala Ala Glu Gln Ala Lys Leu Tyr Gln
            180                 185                 190

Asn Leu Asn Ala Tyr Val Ser Val Gly Thr Ser Thr Leu Asn Gln Arg
        195                 200                 205

Ser Ile Pro Lys Ile Ala Thr Arg Pro Lys Val Asn Gly Gln Ser Gly
    210                 215                 220

Arg Met Glu Phe Phe Trp Thr Ile Leu Arg Pro Asn Asp Thr Ile Ser
225                 230                 235                 240

Phe Glu Ser Thr Gly Asn Phe Ile Ala Pro Glu Tyr Ala Tyr Lys Ile
                245                 250                 255

Val Lys Lys Gly Asp Ser Ala Ile Met Arg Ser Glu Leu Glu Tyr Gly
            260                 265                 270

Asn Cys Asp Thr Lys Cys Gln Thr Pro Leu Gly Ala Ile Asn Ser Ser
        275                 280                 285

Met Pro Phe His Asn Val His Pro Leu Thr Ile Gly Glu Cys Pro Lys
    290                 295                 300

Tyr Val Lys Ser Asp Lys Leu Val Leu Ala Thr Gly Met Arg Asn Val
305                 310                 315                 320

Pro Gln Lys Lys Lys Arg Gly Leu Phe Gly Ala Ile Ala Gly Phe Ile
                325                 330                 335

Glu Gly Gly Trp Gln Gly Met Val Asp Gly Trp Tyr Gly Tyr His His
            340                 345                 350
```

```
Ile Asn Gly Gln Gly Ser Gly Tyr Ala Ala Asp Lys Lys Ser Thr Gln
        355                 360                 365

Lys Ala Ile Asp Gly Ile Thr Asn Lys Val Asn Ser Ile Ile Asp Lys
    370                 375                 380

Met Asn Thr Gln Phe Glu Ala Val Gly Arg Glu Phe Asn Asn Leu Glu
385                 390                 395                 400

Arg Arg Ile Glu Asn Leu Asn Lys Lys Met Glu Asp Gly Phe Ile Asp
                405                 410                 415

Val Trp Thr Tyr Asn Ala Glu Leu Leu Val Leu Met Glu Asn Glu Arg
            420                 425                 430

Thr Leu Asp Leu His Asp Ser Asn Val Lys Asn Leu Tyr Asp Lys Val
        435                 440                 445

Arg Leu Gln Leu Arg Asp Asn Ala Lys Glu Leu Gly Asn Gly Cys Phe
    450                 455                 460

Glu Phe Tyr His Lys Cys Asp Asn Glu Cys Met Glu Ser Val Arg Asn
465                 470                 475                 480

Gly Thr Tyr Asn Tyr Pro Lys Tyr Ser Glu Ser Gly Gly Ser Pro Ala
                485                 490                 495

Asn Ser Thr Val Leu Ser Phe Cys Ala Phe Ala Val Asp Pro Ala Lys
            500                 505                 510

Ala Tyr Lys Asp Tyr Leu Ala Ser Gly Gly Gln Pro Ile Thr Asn Cys
        515                 520                 525

Val Lys Met Leu Cys Thr His Thr Gly Thr Gly Gln Ala Ile Thr Val
    530                 535                 540

Thr Pro Glu Ala Asn Met Asp Gln Glu Ser Phe Gly Gly Ala Ser Cys
545                 550                 555                 560

Cys Leu Tyr Cys Arg Cys His Ile Asp His Pro Asn Pro Lys Gly Phe
                565                 570                 575

Cys Asp Leu Lys Gly Lys Tyr Val Gln Ile Pro Thr Thr Cys Ala Asn
            580                 585                 590

Asp Pro Val Gly Phe Thr Leu Arg Asn Thr Val Cys Thr Val Cys Gly
        595                 600                 605

Met Trp Lys Gly Tyr Gly Cys Ser
    610                 615


<210> SEQ ID NO 3
<211> LENGTH: 216
<212> TYPE: PRT
<213> ORGANISM: SARS coronavirus

<400> SEQUENCE: 3

Glu Ala Ile Val Asn Ala Gln Pro Lys Cys Asn Pro Asn Leu His Tyr
1               5                   10                  15

Trp Thr Thr Gln Asp Glu Gly Ala Ala Ile Gly Leu Ala Trp Ile Pro
            20                  25                  30

Tyr Phe Gly Pro Ala Ala Glu Gly Ile Tyr Thr Glu Gly Leu Met His
        35                  40                  45

Asn Gln Asp Gly Leu Ile Cys Gly Leu Arg Gln Leu Ala Asn Glu Thr
    50                  55                  60

Thr Gln Ala Leu Gln Leu Phe Leu Arg Ala Thr Thr Glu Leu Arg Thr
65                  70                  75                  80

Phe Ser Ile Leu Asn Arg Lys Ala Ile Asp Phe Leu Leu Gln Pro Ala
                85                  90                  95

Asn Ser Thr Val Leu Ser Phe Cys Ala Phe Ala Val Asp Pro Ala Lys
```

-continued

```
            100                 105                 110

Ala Tyr Lys Asp Tyr Leu Ala Ser Gly Gly Gln Pro Ile Thr Asn Cys
        115                 120                 125

Val Lys Met Leu Cys Thr His Thr Gly Thr Gly Gln Ala Ile Thr Val
    130                 135                 140

Thr Pro Glu Ala Asn Met Asp Gln Glu Ser Phe Gly Gly Ala Ser Cys
145                 150                 155                 160

Cys Leu Tyr Cys Arg Cys His Ile Asp His Pro Asn Pro Lys Gly Phe
                165                 170                 175

Cys Asp Leu Lys Gly Lys Tyr Val Gln Ile Pro Thr Thr Cys Ala Asn
            180                 185                 190

Asp Pro Val Gly Phe Thr Leu Arg Asn Thr Val Cys Thr Val Cys Gly
        195                 200                 205

Met Trp Lys Gly Tyr Gly Cys Ser
    210                 215


<210> SEQ ID NO 4
<211> LENGTH: 451
<212> TYPE: PRT
<213> ORGANISM: SARS coronavirus

<400> SEQUENCE: 4

Pro Ala Asn Ser Thr Val Leu Ser Phe Cys Ala Phe Ala Val Asp Pro
1               5                   10                  15

Ala Lys Ala Tyr Lys Asp Tyr Leu Ala Ser Gly Gly Gln Pro Ile Thr
            20                  25                  30

Asn Cys Val Lys Met Leu Cys Thr His Thr Gly Thr Gly Gln Ala Ile
        35                  40                  45

Thr Val Thr Pro Glu Ala Asn Met Asp Gln Glu Ser Phe Gly Gly Ala
    50                  55                  60

Ser Cys Cys Leu Tyr Cys Arg Cys His Ile Asp His Pro Asn Pro Lys
65                  70                  75                  80

Gly Phe Cys Asp Leu Lys Gly Lys Tyr Val Gln Ile Pro Thr Thr Cys
                85                  90                  95

Ala Asn Asp Pro Val Gly Phe Thr Leu Arg Asn Thr Val Cys Thr Val
            100                 105                 110

Cys Gly Met Trp Lys Gly Tyr Gly Cys Ser Gly Gly Ser Met Ala Gly
        115                 120                 125

Leu Asn Pro Ser Gln Arg Arg Glu Val Val Ser Leu Ile Leu Ser Leu
    130                 135                 140

Thr Ser Asn Val Asn Ile Ser His Gly Asp Leu Thr Pro Ile Tyr Glu
145                 150                 155                 160

Arg Leu Thr Asn Leu Glu Ala Ser Thr Glu Leu Leu His Arg Ser Ile
                165                 170                 175

Ser Asp Ile Ser Thr Thr Val Ser Asn Ile Ser Ala Asn Leu Gln Asp
            180                 185                 190

Met Thr His Thr Leu Asp Asp Val Thr Ala Asn Leu Asp Gly Leu Arg
        195                 200                 205

Thr Thr Val Thr Ala Leu Gln Asp Ser Val Ser Ile Leu Ser Thr Asn
    210                 215                 220

Val Thr Asp Leu Thr Asn Arg Ser Ser Ala His Ala Ala Ile Leu Ser
225                 230                 235                 240

Ser Leu Gln Thr Thr Val Asp Gly Asn Ser Thr Ala Ile Ser Asn Leu
                245                 250                 255
```

-continued

```
Lys Ser Asp Ile Ser Ser Asn Gly Leu Ala Ile Thr Asp Leu Gln Asp
            260                 265                 270

Arg Val Lys Ser Leu Glu Ser Thr Ala Ser His Gly Leu Ser Phe Ser
        275                 280                 285

Pro Pro Leu Ser Val Ala Asp Gly Val Val Ser Leu Asp Met Asp Pro
    290                 295                 300

Tyr Phe Cys Ser Gln Arg Val Ser Leu Thr Ser Tyr Ser Ala Glu Ala
305                 310                 315                 320

Gln Leu Met Gln Phe Arg Trp Met Ala Arg Gly Thr Asn Gly Ser Ser
                325                 330                 335

Asp Thr Ile Asp Met Thr Val Asn Ala His Cys His Gly Arg Arg Thr
            340                 345                 350

Asp Tyr Met Met Ser Ser Thr Gly Asn Leu Thr Val Thr Ser Asn Val
        355                 360                 365

Val Leu Leu Thr Phe Asp Leu Ser Asp Ile Thr His Ile Pro Ser Asp
    370                 375                 380

Leu Ala Arg Leu Val Pro Ser Ala Gly Phe Gln Ala Ala Ser Phe Pro
385                 390                 395                 400

Val Asp Val Ser Phe Thr Arg Asp Ser Ala Thr His Ala Tyr Gln Ala
                405                 410                 415

Tyr Gly Val Tyr Ser Ser Ser Arg Val Phe Thr Ile Thr Phe Pro Thr
            420                 425                 430

Gly Gly Asp Gly Thr Ala Asn Ile Arg Ser Leu Thr Val Arg Thr Gly
        435                 440                 445

Ile Asp Thr
    450


<210> SEQ ID NO 5
<211> LENGTH: 498
<212> TYPE: PRT
<213> ORGANISM: SARS coronavirus

<400> SEQUENCE: 5

Pro Ala Asn Ser Thr Val Leu Ser Phe Cys Ala Phe Ala Val Asp Pro
1               5                   10                  15

Ala Lys Ala Tyr Lys Asp Tyr Leu Ala Ser Gly Gly Gln Pro Ile Thr
            20                  25                  30

Asn Cys Val Lys Met Leu Cys Thr His Thr Gly Thr Gly Gln Ala Ile
        35                  40                  45

Thr Val Thr Pro Glu Ala Asn Met Asp Gln Glu Ser Phe Gly Gly Ala
    50                  55                  60

Ser Cys Cys Leu Tyr Cys Arg Cys His Ile Asp His Pro Asn Pro Lys
65                  70                  75                  80

Gly Phe Cys Asp Leu Lys Gly Lys Tyr Val Gln Ile Pro Thr Thr Cys
                85                  90                  95

Ala Asn Asp Pro Val Gly Phe Thr Leu Arg Asn Thr Val Cys Thr Val
            100                 105                 110

Cys Gly Met Trp Lys Gly Tyr Gly Cys Ser Met Gly Ala Ala Cys Gly
        115                 120                 125

Lys Ser Gln Arg Ala Ala Ala Ala Val Glu Pro Pro Leu Ser Thr Ala
    130                 135                 140

Glu Lys Ala Glu Ala Ala Ala Val Ala Ala Ala Glu His Ser Gln Lys
145                 150                 155                 160

Ala Glu Glu Ala Ala Glu Val Ala Ala Ala Cys Ala Thr Lys Ala Ser
                165                 170                 175
```

```
Ala Glu Ala Ala Val Leu Thr Gly Val Glu Pro Gly Ala Glu Pro Ala
            180                 185                 190

Ala Glu Ala Glu Glu Ala Pro Lys Gln Asn Glu Ile Glu Glu Gln Gln
        195                 200                 205

Thr Thr Thr Ser Pro Ala Gln Thr His Ala Thr Glu Glu Gln Pro Ala
    210                 215                 220

Ala Pro Pro Val Val Pro Leu Ser Asp Ala Asp Ala Gln Val Leu Ala
225                 230                 235                 240

Ala Ala Glu Ala Ala Lys Gln Glu Ala Ala Ser Ser Asn Met Pro Arg
                245                 250                 255

Ala Tyr Leu Phe Tyr Ala Cys Glu Leu Asn Glu Gly Ser Leu Met Met
            260                 265                 270

Gln Trp Thr Thr Thr Gln Ile Thr Glu Glu Asp Met His Ala Lys Asn
        275                 280                 285

Leu Ile Leu Leu Ala Ser Phe Val Pro Ala Lys His Lys Thr Val Ser
    290                 295                 300

Lys Ser Lys Leu Thr Gln Asn Gly Gly Ile Thr Tyr Phe Leu Gln Glu
305                 310                 315                 320

Met Lys Tyr Lys Trp Glu Val Trp Ser Lys Val Gln Arg Gln Ala Tyr
                325                 330                 335

Tyr Gln Gly Trp Ile Lys Phe Val Lys Ala Ala Asp Glu Met Glu Ala
            340                 345                 350

Ser Phe Thr Leu His His Phe Ala Ala Pro Ala Pro Pro Ala Lys Leu
        355                 360                 365

Phe Leu Leu His Thr Gly Pro Ile Glu Asn Lys Val Leu Pro Ala Lys
    370                 375                 380

Glu Glu Glu Pro Phe Asn Val Ser Val Phe Gly Leu Ala Ala Val Thr
385                 390                 395                 400

Pro Pro Ser Pro Pro Tyr Lys Pro Gly Ala Asn Ile Thr Pro Lys Arg
                405                 410                 415

Phe Gly Glu Ile Ala Thr Gly Ala Gly Gly Ala Tyr Met Gln Leu Ser
            420                 425                 430

Arg Arg Gly Gly Asp Ala Ala Phe Asp Glu Lys Glu Val Gln Lys Trp
        435                 440                 445

Leu Ala Ala Asp Gly Leu Gln Met Lys Lys Gly Glu Gly Ile Thr Leu
    450                 455                 460

Asp Ala Ala Gly Gly Tyr Glu Arg Arg Ser Glu Lys Lys Gly Gly Asp
465                 470                 475                 480

Ala Ala Ala Ala Thr Ala Ala Val Glu Ala Glu Pro Thr Lys Val Ser
                485                 490                 495

Gln Asp


<210> SEQ ID NO 6
<211> LENGTH: 366
<212> TYPE: PRT
<213> ORGANISM: SARS coronavirus

<400> SEQUENCE: 6

Pro Ala Asn Ser Thr Val Leu Ser Phe Cys Ala Phe Ala Val Asp Pro
1               5                   10                  15

Ala Lys Ala Tyr Lys Asp Tyr Leu Ala Ser Gly Gly Gln Pro Ile Thr
            20                  25                  30

Asn Cys Val Lys Met Leu Cys Thr His Thr Gly Thr Gly Gln Ala Ile
        35                  40                  45
```

```
Thr Val Thr Pro Glu Ala Asn Met Asp Gln Glu Ser Phe Gly Gly Ala
    50                  55                  60

Ser Cys Cys Leu Tyr Cys Arg Cys His Ile Asp His Pro Asn Pro Lys
65                  70                  75                  80

Gly Phe Cys Asp Leu Lys Gly Lys Tyr Val Gln Ile Pro Thr Thr Cys
                85                  90                  95

Ala Asn Asp Pro Val Gly Phe Thr Leu Arg Asn Thr Val Cys Thr Val
            100                 105                 110

Cys Gly Met Trp Lys Gly Tyr Gly Cys Ser Gly Gly Gly Ser Asp Gly
        115                 120                 125

Glu Leu Thr Leu Ala Tyr Asp Ser Thr Asp Phe Gln Val Thr Glu Asn
    130                 135                 140

Gly Leu Ala Leu Lys Val Ser Pro Thr Gln Thr Pro Leu Thr Arg Ile
145                 150                 155                 160

Ile Ser Met Gly Asn Asn Leu Phe Asp Ser Gly Tyr Glu Ile Phe Ala
                165                 170                 175

Ser Cys Pro Gln Asn Lys Ala Ala Lys Val Ala Gly Tyr Val Tyr Leu
            180                 185                 190

Thr Ser Val Gly Gly Leu Val His Gly Thr Ile Gln Ile Lys Ala Thr
        195                 200                 205

Ala Gly Tyr Trp Phe Thr Gly Gly Asn Ser Val Gln Glu Ser Ile Arg
    210                 215                 220

Phe Gly Leu Val Leu Cys Pro Phe Ser Ala Arg Asp Pro Thr Ala Asn
225                 230                 235                 240

Leu Ser Gly Trp Pro Ala Pro Val Val Trp Ser Gly Asp Ser Asn Thr
                245                 250                 255

Pro Leu Tyr Phe Ala Ala Asn Ala Ile Ser Tyr Thr Asn Asn Arg Val
            260                 265                 270

Asn Leu Ala Val Thr Gly Asn Phe Tyr Lys Glu Glu Thr Glu Leu Pro
        275                 280                 285

Gly Tyr Thr Arg His Ser Phe Cys Pro Thr Gly Thr Thr Gly Met Asn
    290                 295                 300

Phe Thr Gly Gly Asn Leu Tyr Val Cys Pro Cys Thr Val Asn Thr Gly
305                 310                 315                 320

Ala Thr Thr Leu Asn Ala Ile Tyr Met Val Phe Val Ile Thr Gln Ser
                325                 330                 335

Ala Leu Gly Thr Asn Phe Phe Ala Ser Asn Thr Pro Pro Asn Thr Phe
            340                 345                 350

Phe Leu Thr Pro Pro Ile Pro Phe Thr Tyr Val Gly Ala Gln
        355                 360                 365


<210> SEQ ID NO 7
<211> LENGTH: 121
<212> TYPE: PRT
<213> ORGANISM: SARS coronavirus

<400> SEQUENCE: 7

Pro Ala Asn Ser Thr Val Leu Ser Phe Cys Ala Phe Ala Val Asp Pro
1               5                   10                  15

Ala Lys Ala Tyr Lys Asp Tyr Leu Ala Ser Gly Gly Gln Pro Ile Thr
            20                  25                  30

Asn Cys Val Lys Met Leu Cys Thr His Thr Gly Thr Gly Gln Ala Ile
        35                  40                  45

Thr Val Thr Pro Glu Ala Asn Met Asp Gln Glu Ser Phe Gly Gly Ala
```

```
    50                  55                  60

Ser Cys Cys Leu Tyr Cys Arg Cys His Ile Asp His Pro Asn Pro Lys
65                  70                  75                  80

Gly Phe Cys Asp Lys Gly Lys Tyr Val Gln Ile Pro Thr Thr Cys Ala
                85                  90                  95

Asn Asp Pro Val Gly Phe Thr Leu Arg Asn Thr Val Cys Thr Val Cys
            100                 105                 110

Gly Met Trp Lys Gly Tyr Gly Cys Ser
        115                 120


<210> SEQ ID NO 8
<211> LENGTH: 125
<212> TYPE: PRT
<213> ORGANISM: SARS coronavirus

<400> SEQUENCE: 8

Pro Ala Asn Ser Thr Val Leu Ser Phe Cys Ala Phe Ala Val Asp Pro
1               5                   10                  15

Ala Lys Ala Tyr Lys Asp Tyr Leu Ala Ser Gly Gly Gln Pro Ile Thr
            20                  25                  30

Asn Cys Val Lys Met Leu Cys Thr His Thr Gly Thr Gly Gln Ala Ile
        35                  40                  45

Thr Val Thr Pro Glu Ala Asn Met Asp Gln Glu Ser Phe Gly Gly Ala
    50                  55                  60

Ser Cys Cys Leu Tyr Cys Arg Cys His Ile Asp His Pro Asn Pro Lys
65                  70                  75                  80

Gly Phe Cys Asp Leu Lys Gly Lys Tyr Val Gln Ile Pro Thr Thr Cys
                85                  90                  95

Ala Asn Asp Pro Val Gly Phe Thr Leu Arg Asn Thr Val Cys Thr Val
            100                 105                 110

Cys Gly Met Trp Lys Gly Tyr Gly Cys Ser Gly Gly Ser
        115                 120                 125


<210> SEQ ID NO 9
<211> LENGTH: 261
<212> TYPE: PRT
<213> ORGANISM: SARS coronavirus

<400> SEQUENCE: 9

Val Ser Ile Lys Lys Ser Ser Gly Leu Asn Phe Asp Asn Thr Ala Ile
1               5                   10                  15

Ala Ile Asn Ala Gly Lys Gly Leu Glu Phe Asp Thr Asn Thr Ser Glu
            20                  25                  30

Ser Pro Asp Ile Asn Pro Ile Lys Thr Lys Ile Gly Ser Gly Ile Asp
        35                  40                  45

Tyr Asn Glu Asn Gly Ala Met Ile Thr Lys Leu Gly Ala Gly Leu Ser
    50                  55                  60

Phe Asp Asn Ser Gly Ala Ile Thr Ile Gly Asn Lys Asn Asp Asp Lys
65                  70                  75                  80

Leu Thr Leu Trp Thr Pro Asp Pro Ser Pro Asn Cys Arg Ile His Ser
                85                  90                  95

Asp Asn Asp Cys Lys Phe Thr Leu Val Leu Thr Lys Cys Gly Ser Gln
            100                 105                 110

Val Leu Ala Thr Val Ala Ala Leu Ala Val Ser Gly Asp Leu Ser Ser
        115                 120                 125

Met Thr Gly Thr Val Ala Ser Val Ser Ile Phe Leu Arg Phe Asp Gln
```

-continued

```
    130                 135                 140

Asn Gly Val Leu Met Glu Asn Ser Ser Leu Lys Lys His Tyr Trp Asn
145                 150                 155                 160

Phe Arg Asn Gly Asn Ser Thr Asn Ala Asn Pro Tyr Thr Asn Ala Val
                165                 170                 175

Gly Phe Met Pro Asn Leu Leu Ala Pro Lys Thr Gln Ser Gln Thr Ala
            180                 185                 190

Lys Asn Asn Ile Val Ser Gln Val Tyr Leu His Gly Asp Lys Thr Lys
        195                 200                 205

Pro Met Ile Leu Thr Ile Thr Leu Asn Gly Thr Ser Glu Ser Thr Glu
    210                 215                 220

Thr Ser Glu Val Ser Thr Tyr Ser Met Ser Phe Thr Trp Ser Trp Glu
225                 230                 235                 240

Ser Gly Tyr Thr Thr Glu Thr Phe Ala Thr Asn Ser Tyr Thr Phe Ser
                245                 250                 255

Tyr Ile Ala Gln Glu
            260
```